(12) United States Patent
Gareau

(10) Patent No.: US 10,001,635 B2
(45) Date of Patent: *Jun. 19, 2018

(54) RAPID CONFOCAL MICROSCOPY TO SUPPORT SURGICAL PROCEDURES

(71) Applicants: SLOAN KETTERING INSTITUTE FOR CANCER RESEARCH, New York, NY (US); OREGON HEALTH & SCIENCE UNIVERSITY, Portland, OR (US)

(72) Inventor: Daniel S. Gareau, Providence, RI (US)

(73) Assignees: Sloan Kettering Institute for Cancer Research, New York, NY (US); Oregon Health and Science University, Portland, OR (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/868,042

(22) Filed: Sep. 28, 2015

(65) Prior Publication Data

US 2016/0018632 A1 Jan. 21, 2016

Related U.S. Application Data

(63) Continuation of application No. 13/055,806, filed as application No. PCT/US2009/051731 on Jul. 24, 2009, now Pat. No. 9,176,310.

(60) Provisional application No. 61/083,803, filed on Jul. 25, 2008.

(51) Int. Cl.
| | |
|---|---|
| *G02B 21/36* | (2006.01) |
| *G01N 1/30* | (2006.01) |
| *G01N 21/64* | (2006.01) |
| *G02B 21/00* | (2006.01) |
| *G02B 21/16* | (2006.01) |
| *H04N 5/225* | (2006.01) |
| *H04N 9/797* | (2006.01) |

(52) U.S. Cl.
CPC ............ *G02B 21/367* (2013.01); *G01N 1/30* (2013.01); *G01N 21/6458* (2013.01); *G02B 21/008* (2013.01); *G02B 21/0064* (2013.01); *G02B 21/0076* (2013.01); *G02B 21/16* (2013.01); *H04N 5/2256* (2013.01); *H04N 9/797* (2013.01); *G01N 2001/302* (2013.01)

(58) Field of Classification Search
CPC ................ G01N 21/6458; G01N 1/30; G01N 2001/302; G02B 21/0064; G02B 21/0076; G02B 21/008; G02B 21/367; G02B 21/16; H04N 5/2256; H04N 9/797
See application file for complete search history.

(56) References Cited

U.S. PATENT DOCUMENTS

| | | | |
|---|---|---|---|
| 4,805,543 A | 2/1989 | Schwab et al. | |
| 5,161,053 A | 11/1992 | Dabbs | |
| 5,532,874 A | 7/1996 | Stein | |
| 5,537,247 A | 7/1996 | Xiao | |
| 5,825,020 A | 10/1998 | Hansma et al. | |
| 6,194,551 B1 | 2/2001 | Kerschmann et al. | |
| 6,195,451 B1 | 2/2001 | Kerschmann et al. | |
| 6,310,342 B1 | 10/2001 | Braunstein et al. | |
| 6,449,087 B2 | 9/2002 | Ogino | |
| 6,580,518 B2 | 6/2003 | Eda et al. | |
| 6,661,509 B2 | 12/2003 | Deck et al. | |
| 2003/0052280 A1 | 3/2003 | Foster et al. | |

OTHER PUBLICATIONS

Molecular Probes Handbook—chapter 8.1, "Nucleic acid stains", published online on Mar. 1, 2003 (at the web—http://www.mobitec. de/probes/docs/sections/0801.pdf), pp. 269-287.*
Frey T., "Nucleic acid dyes for detaction of apoptosis in live cells", Cytometry, 1995, vol. 21, pp. 265-274.*
Molecular Probes Product information, "Syto® Green-fluorescent nucleic acid stains", published on Aug. 11, 2003, pp. 1-3.*
Corcuff, P., et al., "Confocual laser microscopy of the in vivo human skin revisited," SPIE Conference on Three-Dimensional and Multidimensional Microscopy: Image Acquisition and Processing VI, San Jose, CA, Jan. 1999, pp. 73-81, vol. 3605, Publisher: SPIE.
EPO, Examination Report for the corresponding EP application No. 09801090.3, dated Feb. 3, 2016, pp. 1-5.
Al-Arashi et al., "Multimodal Confocal Microscopy for Diagnosing Nonmelanoma Skin Cancers", "Lasers in Surgery and Medicine", 2007, pp. 696-705, vol. 39.
Gareau et al., "Confocal Mosaicing of Basal Cell Carcinomas in Mohs Surgical Skin Excisions", Jan. 23, 2007, pp. 1-1, Publisher: SPIE Photonics West, 2007 Poster Session, XP002651347, San Jose Convention Center.
Gareau, Daniel S., "Feasibility of digitally stained multimodal confocal mosaics to simulate histopathology", May 2009, pp. 1-5, vol. 14, No. 3, Publisher: Jouranl of Biomedical Optics.

(Continued)

*Primary Examiner* — Satyendra K Singh
(74) *Attorney, Agent, or Firm* — Eugene J. Molinelli; Beusse Wolter Sanks & Maire

(57) ABSTRACT

One embodiment of techniques for confocal microscopy includes illuminating a spot on a surface of a biological sample. A first emission intensity from the spot is detected in a first range of optical properties; and a second emission intensity in a second ranges A pixel that corresponds to the spot is colored using a linear combination of the first and second emission intensities. Sometimes, the pixel is colored to approximate a color produced by histology. In some embodiments, a surface of a sample is contacted with a solution of a nucleus dye. Then, a spot is illuminated with a laser beam of wavelength about 488 nanometers (nm). Fluorescence emission intensity is detected above about 500 nm. Sometimes, a certain illumination correction is applied. In some embodiments, a sample holder that compresses a sample is removable from a stage that is fixed with respect to a focal plane of the microscope.

9 Claims, 22 Drawing Sheets

(56) References Cited

OTHER PUBLICATIONS

Li et al., "Dual Mode Reflectance and Fluorescence Confocal Laser Scanning Microscopy for In Vivo Imaging Melanoma Progression in Murine Skin", "The Journal of Investigative Dermatology", Oct. 1, 2005, pp. 798-804, vol. 125, No. 4.
EPO, "The extended European search report for corresponding EP application No. 09801090.3-1234", dated Aug. 9, 2011, pp. 1-16, Published in: Netherlands.
Patel et al. , "Confocal reflectance mosaicing of basal cell carcinomas in Mohs surgical skin excisions.", "Journal of Biomedical Optics", May 31, 2007, pp. 10, vol. 12, No. 3, Publisher: Society of Photographic Instrumentation Engineers , Published in: Bellingham, WA, USA.
Blaine Copenheaver, "International Search Report and Written opinion", dated Jan. 28, 2010 for WO2010011953.
EPO: Examination Report, European Patent Application No. 09801090.3, dated Apr. 3, 2017, six pages.
Meyer, L.E., et al., "In vivo confocal scanning laser microscopy: comparison of the reflectance and fluorescence mode by imaging human skin," Journal of Biomedical Optics 2006, pp. 044012-1-044012-7, vol. 11, No. 4.
Berman, D., et al., "Grading melanocytic dysplasia in parrafix wax embedded tissue by the nucleic acid index," J. Clin. Pathol., 2005, pp. 1206-1210, vol. 58.
Bio-Rad, "PureBlu Hoeschst 33342 Nuclear Staining Dye," Bio-Rad Laboratories, Inc., http://www.bio-rad.com/webroot/web/pdf/lsr/literature/10043283.pdf, undated, two pages, 2014.
Brink, P., et al., "A model for the diffusion of fluorescent probes in the septate giant axon of earthworm," Biophys. J., Aug. 1985, pp. 299-309, vol. 48.
Chazotte, B., "Labeling the nucleus with fluorescent dyes for imaging," CSH Protocols; 2008; doi:10.1101/pdb. prot4950, pp. 1-4.
Conti, F., et al., "Changes in extrinsic fluorescence in squid axons during voltage clamp," Science, Sep. 25, 1970, pp. 1322-1324, vol. 169.
Daniel, A., et al., "Identification of Marker Chromosomes in Thirteen Patients Uing FISH Probing," Am. J. Med. Genet., 1994, pp. 8-18, vol. 53.
Dutt, M., "Staining of DNA-phosphate groups with a mixture of azure A and acridine yellow," Microsc. Acta, Nov. 1979, vol. 82, No. 3, Abstract only.
Latt, S., "Spectral studies on 33258 Hoechst and related bisbenzimidazole dyes useful for fluorescent detection of deoxyribonucleic acid synthesis," J. Histochem. Cytochem., 1976, pp. 24-33, vol. 24, No. 1.
Martin, R., et al., "DNA labeling in living cells," Cytometry A, Sep. 2005, pp. 45-52, vol. 67, No. 1.
Matzke, K., "The Acridine Dyes: Their Purification, Physiochemical, and Cytochemical Properties," Histochemistry, Oct. 1976, pp. 73-79, vol. 49, No. 1, Publisher: Springer-Verlag.
Moore, G., "The clinical use of fluorescein in neurosurgery; the localization of brain tumors," J. Neurosurg., Jul. 5, 1948, pp. 392-398, vol. 5, No. 4.
Quadrifoglio, F., et al., "Calorimetry of DNA-dye interactions in aqueous solution," Biophys. Chem., 1974, pp. 319-324, vol. 1, Publisher: North-Holland Publishing Company.
Szabo, G., et al., "Flow Cytometric Analysis of the Uptake of Hoechst 33342 Dye by Human Lymphocytes," Cytometry, 1981, pp. 20-23, vol. 2, No. 1.
Vinegar, R., "Metachromatic differential fluorochroming of living and dead ascites tumor cells with acridine orange," Cancer Research, Oct. 1956, pp. 900-906, vol. 16, No. 9.

\* cited by examiner

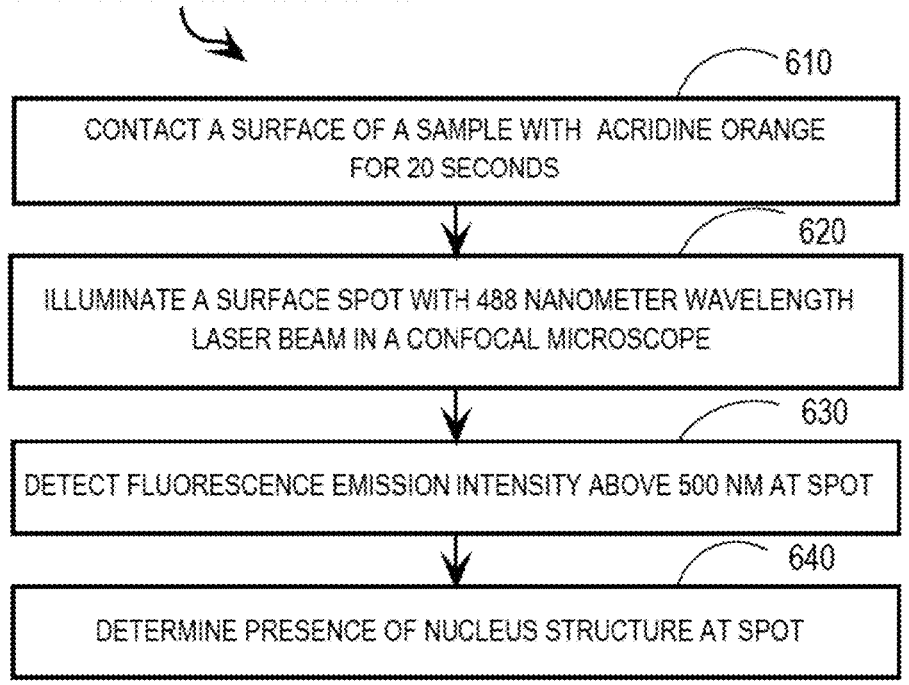

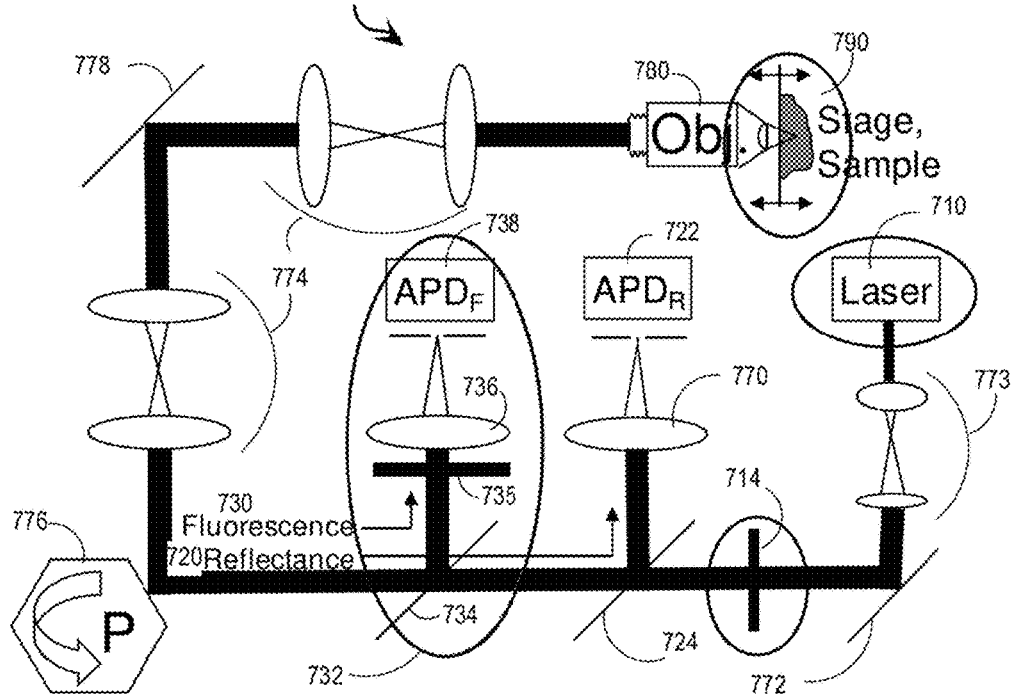

1000 FLUORESCENCE IMAGE

1100 REFLECTANCE IMAGE

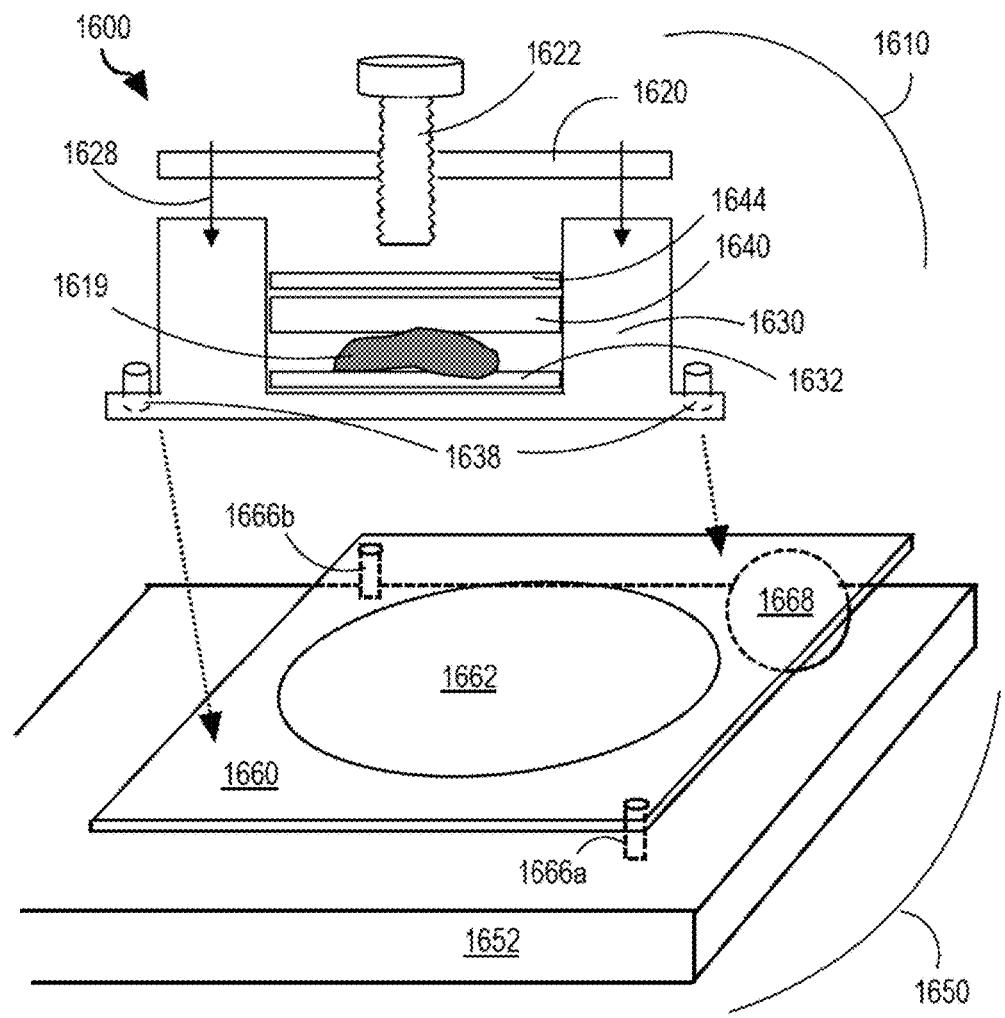

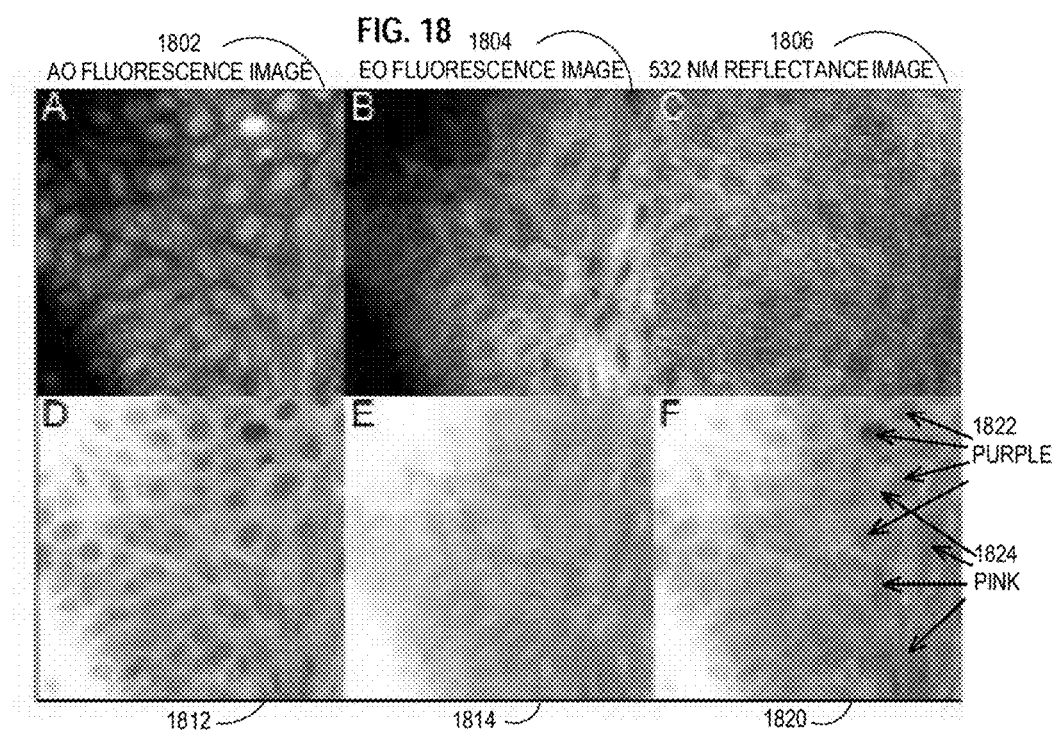

RAPID CONFOCAL MICROSCOPY TO SUPPORT SURGICAL PROCEDURES

CROSS-REFERENCE TO RELATED APPLICATIONS

This application claims benefit as a Continuation of application Ser. No. 13/055,806, filed Jan. 25, 2011 the entire contents of which are hereby incorporated by reference as if fully set forth herein, under 35 U.S.C. § 120, which is a 371 national stage application of Patent Cooperation Treaty international Patent Appln. PCT/US2009/051731 filed Jul. 24, 2009, the entire contents of which are hereby incorporated by reference as if fully set forth herein, which claims benefit of Provisional Appln. 61/083,803, filed Jul. 25, 2008, the entire contents of which are hereby incorporated by reference as if fully set forth herein, under 35 U.S.C. § 119.

BACKGROUND

Embodiments of the present invention relate to confocal microscopy with fluorescence to support surgical procedures, such as incremental surgery to remove tumors that are not naturally visible to a surgeon. In some embodiments, multimodal confocal microscopy is used to render images that emulate frozen histology sections.

Several surgical procedures to remove tumors involve cell morphology that is difficult to discern with the unaided eye. In such circumstances, successive incremental excisions are performed, and each sample of excised tissue is subjected to histological examination to determine the remaining extent of the tumor. The position and extent of the tumor evident in the histology sections is used to guide the next excision. However, the procedure for preparing the histology sections is tedious and time consuming, often exceeding 30 minutes per section. Thus, surgical procedures that rely on such histology sections can extend to two hours and more, increasing the exposure of patient to infection and undesirable consequences of surgery, and limiting the availability of surgeons for other procedures.

For example, Mohs surgery for the removal of basal cell carcinoma (BCC) in skin often requires several excisions. After each excision, a frozen histology section is prepared while the surgeon waits. The location and extent of the tumor evident in the frozen histology section guides the next excision. The preparation of the frozen histology section, including staining to enhance visibility of certain structures, is tedious and takes 24 to 40 minutes. Thus the surgery usually lasts several hours.

Other surgical procedures that involve viewing histology of incremental excisions include the removal of oral mucosal lesions, thyroid nodules, parathyroid glands and bone, and include needle core biopsies and lumpectomies of the breast, and inter-operative biopsies of liver and bladder, among others.

Confocal microscopy is capable of directly observing, in real time, very small structures in a very small field of view and can directly observe tumors in excised tissue. A confocal microscope achieves very high resolution by using the same objective lens to focus both a parallel beam of incident light and the resulting emitted light at the same small spot on or near the surface of target tissue. For example, a typical confocal microscope using an objective lens that magnifies an object in the focal plane 30 times (30×) resolves spots that are about half of a micron ($\mu m$, 1 $\mu m = 10^{-6}$ meters) across, sufficient to resolve morphology of a nucleus of a cell, which is about 10 microns. A field of view is obtained by scanning the confocal spot across the tissue by changing the angle of the incident beam of light. In an example confocal microscope, the field of view is about 400 $\mu m$, and includes about 1024 rows and 1,024 columns of pixels, for an individual image of about one million pixels.

This confocal microscope field of view is small compared to the field of view of histology sections. A histology section often includes a field of view that is millimeters to tens of millimeters (mm, 1 mm=$10^{-3}$ meters) across, about forty times larger than the confocal microscope field of view. For example, in Mohs surgery, a 2× magnification is used in a standard light microscope to view a 12 mm by 12 mm (12×12 mm) portion of the frozen histology section.

SOME EXAMPLE EMBODIMENTS

Techniques are provided for confocal microscopy, which offer one or more advantages over prior art approaches.

In one set of embodiments, an apparatus for mounting excised tissue for examination by a confocal microscope includes a stage and a sample holder. The stage is configured to be adjusted to align a surface of the stage with a focal plane of a confocal microscope. The sample holder includes a transparent plate configured to compress a sample of excised tissue. The sample holder is removeably mounted to the stage so that the transparent plate is flush with the surface that is aligned with the focal plane of the confocal microscope without further adjustment of the stage.

In another set of embodiments, an apparatus includes a support member that includes an axial through hole with a non-circular cross section. A transparent plate is fixed at one end of the axial through hole. A plate has a non-circular cross section that matches the non-circular cross section of the axial through hole. A piston is configured to drive the plate within the axial through hole toward the transparent plate and compress a sample of excised tissue between the plate and the transparent plate. In some of these embodiments, a gel is configured to be placed between the plate and the excised tissue during compression of the excised tissue between the plate and the transparent plate. The gel, when compressed, holds the compressed excised tissue against the transparent plate to prevent lateral motion of the compressed excised tissue with respect to the transparent plate.

In another set of embodiments, a method includes determining a z position of maximum reflectance at each of three horizontal positions for a moving stage. One or more set screws on the stage are controlled with a micropositioning actuator so that adjusted z positions for the three horizontal positions are parallel to a focal plane of a confocal microscope.

In another set of embodiments, a method for automatically correcting a focal plane of a confocal microscope includes determining a z position of maximum reflectance at each of three horizontal positions for a moving stage. A plane through the z positions of maximum reflectance at the three horizontal positions is determined. A z location for an objective lens is determined at each horizontal position for the moving stage so that the objective lens is focused a consistent distance from the plane. A vertical position of the objective lens is controlled with a micropositioning actuator to match the z location for the objective lens corresponding to a current horizontal position of the moving stage.

In another set of embodiments, a method for merging overlapping images from a confocal microscope includes determining a translation of a first image with respect to a second image that minimizes a difference of light intensity in an overlapping region between the first image and the second image. Light intensities from one pixel in the overlapped region of the first image and a corresponding pixel in the translated second image are averaged to produce a merged image.

In another set of embodiments, a method for correcting illumination includes receiving a set of multiple images from a confocal microscope. Each image includes a two dimensional array of pixels located by a row number a column number, and each image covers a different portion of a single sample. A pixel average intensity is determined for each pixel location by averaging intensity values at the pixel location over every image of the set. A pixel illumination correction based on the pixel average intensity for each pixel location is applied to every pixel at the pixel location in the set of images.

In another set of embodiments, a method for detecting cell nuclei with a confocal microscope includes contacting a surface of a sample of excised tissue with a solution of acridine orange. A spot on the surface of the excised sample is illuminated with a laser beam of wavelength about 488 nanometers (nm, 1 nm=$10^{-9}$ meters). Fluorescent emission intensity from the spot is detected in a wavelength range above about 500 nm.

In another set of embodiments, a method for presenting a multimodal image includes illuminating a spot on a surface of a biological sample with a light beam using a confocal microscope. A first emission intensity from the spot is detected within a first range of optical properties, such as wavelength, polarization or phase, or some combination. A second emission intensity from the spot is detected within a second range of optical properties. A pixel that corresponds to the spot in an image is colored using a linear combination of the first emission intensity detected from the spot and the second emission intensity detected from the spot. In some of these embodiments, the pixel is colored to approximate a color produced by a histology section for tissue at the spot. In some of these embodiments, at least one detected emission intensity is reflectance.

In another set of embodiments, an apparatus for modulating wavelength of irradiance in a confocal microscope having a plurality of lasers, includes a detector for tracking each cycle of movement of a mirror used to scan one direction of a focal plane of the confocal microscope with irradiance. A deflection component differentially deflects a corresponding plurality of laser beams from the plurality of lasers. A controller causes the deflection component to deflect a different laser beam of the plurality of laser beams onto the mirror with each cycle. In some of these embodiments, the deflection component is an acousto-optic deflector.

In one or more other embodiments, an apparatus, system or computer-readable medium is configured to perform one or more steps of the above methods.

BRIEF DESCRIPTION OF THE DRAWINGS

The present invention is illustrated by way of example, and not by way of limitation, in the figures of the accompanying drawings and in which like reference numerals refer to similar elements and in which:

FIG. 6 is a flow diagram that illustrates at a high level a method for obtaining fluorescence that provides high contrast to cell nuclei with a fast stain, according to an embodiment;

FIG. 7A is a block diagram that illustrates a multi modal reflectance/fluorescence confocal microscope, according to an embodiment;

FIG. 16A is a block diagram that illustrates an adjustable stage and removable sample holder, according to another embodiment;

FIG. 18 is a graph that illustrates coloring of pixels from two fluorescence images to approximate histology, according to an embodiment.

DETAILED DESCRIPTION

Figure 1:
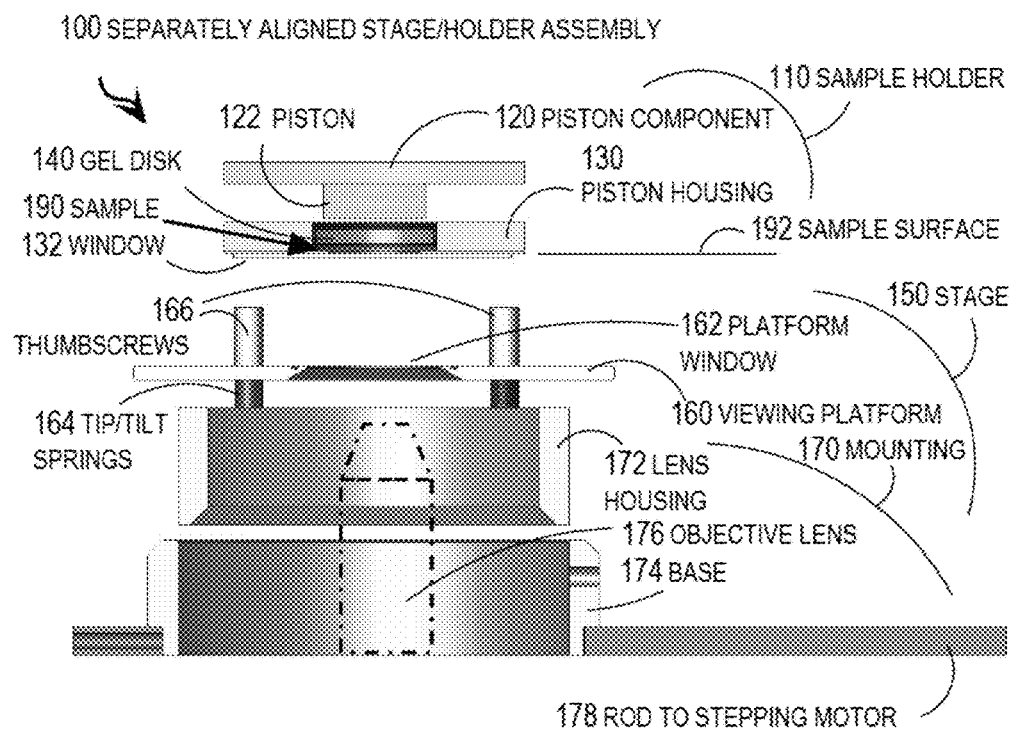
FIG. 1 is a block diagram that illustrates an example apparatus for fixing a sample in a focal plane of a confocal microscope, according to an embodiment.

Techniques are described for rapid confocal microscopy, such as is useful in surgical procedures. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

For convenience, the term emission is used herein to mean any light from an object, whether generated by the object, such as fluorescence, or reflected from the object. Some embodiments of the invention are described below in the context of Mohs surgery for incremental excision of BCCs. However, the invention is not limited to this context. In other embodiments rapid confocal microscopy is used to support other incremental surgeries and intra-operative biopsies for a variety of surgeries to treat a variety of disorders, including, and thus not limited to, removal of oral mucosal lesions, thyroid nodules, parathyroid glands and bone, and include needle core biopsies and lumpectomies of the breast, and inter-operative biopsies of liver and bladder.

1. Overview

It was determined that confocal microscopes configured with a stepping stage are able to collect multiple images in two dimensions that can be put together in a mosaic to provide a larger field of view, comparable to a field of view provided by histology sections and relied upon during incremental surgeries. (See Patel Y. G., Nehal K. S., Aranda I., Li Y., Halpern A. C., Rajadhyaksha M., "Confocal reflectance mosaicing of basal cell carcinomas in Mohs surgical skin excisions," *J. Biomed. Optics*, vol. 12, No. 3, p 034027, 2007, the entire contents of which are hereby incorporated by reference as if fully set forth herein, except for any use of terminology that is not consistent with the use of terms defined herein.)

Furthermore, the inventor has determined that fluorescent confocal microscopy images arranged in a mosaic can support Mohs surgery in significantly less time (9 minutes or less) than frozen histology sections (24 minutes or more). See D. S. Gareau, Y. G. Patel, Y. Li, I. Aranda, A. C. Halpern, K. S. Nehal, and M. Rajadhyaksha, "Confocal mosaicing microscopy in skin excisions: a demonstration of rapid surgical pathology," *Journal of Microscopy*, vol. 233, num. 1, pp 149-159, January 2009 (hereinafter Gareau), the entire contents of which are hereby incorporated by reference as if fully set forth herein, except for any use of terminology that is not consistent with the use of terms defined herein.

Furthermore the inventor has determined improvements to sample fixation, illumination correction, image merging and multimodal operation that further speed or enhance the results in support of surgical procedures in general, and Mohs surgery in particular.

The various embodiments that support rapid confocal microscopy to support surgical procedures are described in more detail in the following sections: 2. Tissue fixation apparatus; 3. Image merging for mosaic; 4. Illumination correction; 5. Fast staining for nuclear fluorescence contrast; and, 6. Multimodal image presentation. Computational hardware to implement some methods in some embodiments is described in section 7, and section 8 indicates extensions and alternatives.

These techniques speed or enhance the rapid formation of images. Using these techniques images can be made available for incremental surgery or intra-operative biopsies well before histology sections could be made available. Thus these techniques have the potential to replace the use of histological sections during surgery and thereby lower costs to hospitals of performing such surgeries and decrease the dangers of surgery to the patient.

2. Tissue Fixation Apparatus

Some improvements were developed in fixing tissue in a focal plane for confocal microscopy. First, a sample holder for compressing the sample against a viewing window is separated from a stage that is in fixed alignment (though not necessarily parallel alignment) with a focal plane of an objective lens of the confocal microscope. Second a sample holder is configured to avoid twisting the sample while compressing the sample against the viewing window.

The sample holder is separated from the stage because it can take several minutes to adjust thumbscrews to align a stage with the focal plane of the objective lens. In order to save time during a surgical procedure, the inventors configured the stage to be aligned ahead of time. After surgery starts and a sample is collected, the sample is compressed in a separate sample holder in a few seconds. The sample holder is then placed on the pre-aligned stage, where the sample holder can easily be moved laterally to center on the region of interest in another few seconds. Either the stage is parallel to the focal plane or the vertical deviations as a function of horizontal position can be compensated by vertically stepping the objective lens. Thus, without further adjustment, confocal microscopy image collection can begin.

Thus, according to some embodiments, an apparatus for mounting excised tissue for examination by a confocal microscope includes a stage and a sample holder. The stage is configured to fix a surface of the stage with respect to a focal plane of a confocal microscope. The sample holder includes a transparent plate configured to compress a sample of excised tissue. The sample holder is removeably mounted to the stage so that the transparent plate is in known relation to the surface that is in fixed alignment with the focal plane of the confocal microscope without further adjustment of the stage.

FIG. 1 is a block diagram that illustrates an example apparatus 100 for fixing a sample in relation to a focal plane of a confocal microscope, according to an embodiment. The apparatus 100 is a separately aligned stage/holder assembly that includes a sample holder 110 and a separate stage 150. Also shown is a sample 190 for purposes of illustration; however, the sample 190 is not part of the apparatus 100.

Sample holder 110 includes a piston component 120 and a piston housing 130. The piston component 120 includes piston 122. The piston housing 130 includes a through hole and a window 132. The piston 122 travels through the through hole to compress the sample 190 against the window 132 for viewing. In some embodiments, a gel disk 140 is included in the through hole between the sample 190 and the piston 122 to help fix the sample 190 against the window to avoid lateral movement and to cushion the sample 190 from the piston 122. When the piston 122 is inserted in the through hole of housing 132, a surface of the sample is pressed flat against the top surface of the window, as indicated by the sample surface location 192. In an example embodiment, the piston component 120 and the piston housing 130 are made of polycarbonate, the window 132 is made of glass, and the gel disk 140 is made of 3% Agarose gel. In some embodiments, the gel is specially shaped to include a large convex surface to press the center of the excision first, and a small concave surface to pin the excision in the center of the window.

Stage 150 includes a viewing platform 160 and a platform mounting 170. The platform mounting 170 includes a lens housing 172, a base 174, an objective lens 176, and a rod 178. The rod 178 connects the base 174 to a stepping motor so that the lens housing 172, the base 174, and attached platform 160 can be stepped horizontally relative to the objective lens 176 and other optical components (not shown) in both x and y directions. The stepping in x and y directions is performed to collect a two dimensional array of overlapping images that can be merged into a mosaic with a wider field of view than individual images. In some embodiments, the stage includes a second rod (not shown), perpendicular to rod 178, to a second stepping motor so that the lens housing 172, the base 174, and attached platform 160 can be stepped horizontally in a perpendicular direction.

The viewing platform 160 is a plate that includes a window 162. The platform is attached to the lens housing 172 via adjustable thumbscrews 166. The upper surface of the platform 160 is kept flush with the bottom surface of the heads of the thumbscrews 166 by springs 164. As the thumbscrews are tightened or loosened to move down or up, the platform responds. Thus the thumbscrews can be turned to adjust the tilt and tip of the top surface of the viewing platform 160 and its window 162.

When the sample holder is placed on the viewing platform, the viewable surface of the sample 192 is above the upper surface of the platform 160 by at least the thickness of holder window 132. Thus the thumbscrews are adjusted until the focal plane of objective lens 176 is parallel (or near parallel) to and above the upper surface of platform 160 by a desired tissue depth (e.g., 1 mm) plus the thickness of the window 132 and any offset between the window 132 and the bottom of the piston housing (zero in FIG. 1 but non-zero in another embodiment described below with reference to FIG. 2B). In some embodiments, any deviations from parallel can be corrected by vertically stepping the objective lens, as described in more detail below. The adjustment of thumbscrews to set the viewing platform 160 of stage 150 may be performed even before a sample is collected. When a sample is collected, it is placed in holder 110, and compressed against window 132 in just a few seconds. The holder is placed on the surface of platform 160 and moved laterally, parallel to platform 160 until the portion of the sample of interest is centered above the objective lens. Because the stage is already in fixed alignment, imaging of the sample can begin immediately, no further adjustment of thumbscrews 166 is needed.

In the illustrated embodiment, the base 174 is made of brass, the lens housing 172 is made of aluminum, and the platform 160 is made of stainless steel.

In some embodiments, the piston 122 and through hole of piston housing 130 are threaded to move the piston to compress the sample and keep the piston in place when the sample is compressed to the desired degree. Both the piston 122 and the through hole have circular cross sections in these embodiments. However, the twisting of the piston 122 against the gel 140 and sample 190 might distort the surface of the sample against the window 132. Thus in some embodiments, the holder is modified to reduce or eliminate the distortion of the sample when a piston twists as it travels along the through hole.

Figure 2A:
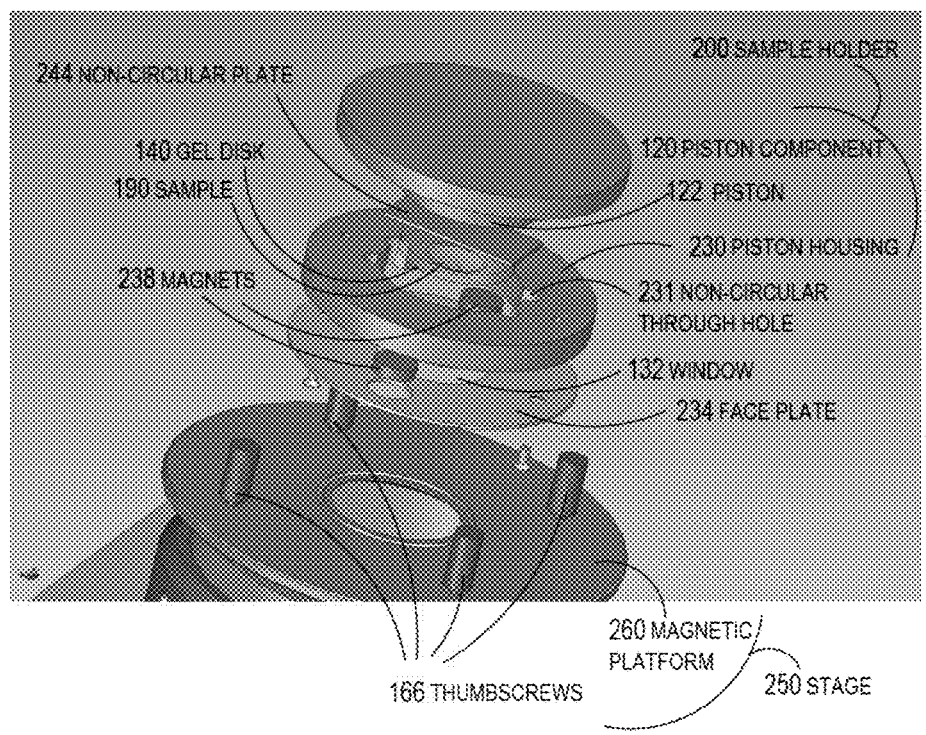
FIG. 2A is a block diagram that illustrates a stage and an exploded view of a sample holder, according to another embodiment.

Thus, in some embodiments, an apparatus includes a piston housing that includes an axial through hole with a non-circular cross section. A transparent plate is fixed at one end of the axial through hole. Another plate has a non-circular cross section that matches the non-circular cross section of the axial through hole. A piston is configured to drive the plate within the axial through hole toward the transparent plate and compress a sample of excised tissue between the plate and the transparent plate. In some of these embodiments, a gel is configured to be placed between the plate and the sample during compression of the sample between the plate and the transparent plate. The gel, when compressed, holds the compressed excised tissue against the transparent plate to prevent lateral motion of the compressed excised tissue with respect to the transparent plate FIG. 2A is a block diagram that illustrates a stage 250 and an exploded view of a sample holder 200, according to one of these embodiments. The sample holder 200 includes a piston component 120 with piston 122, as described above, and a modified piston housing 230. The modified piston housing 230 has a non-circular through hole 231 and a plate 244 with a rectangular cross section that matches the non-circular cross section of the through hole 231. As used herein, a plate cross section matches the through hole cross section if it fits within the cross section and is unable to rotate in the plane of the cross section when disposed inside the through hole. In some embodiments, the plate cross section is the same as the through hole cross section. The deviation from a circular cross section is small enough that threads on the piston 122 engage threads on circular portions of the through hole 231.

Thus when the piston is threaded into the through hole, the plate travels along the axis of the through hole to compress the gel 140 and sample 190, but does not twist and therefore does not distort the gel 140 or sample.

In some embodiments the gel disk 140 is replaced with a gel that has a cross section that matches the cross section of the through hole 231.

In the illustrated embodiment, sample holder 200 includes magnets 238. The magnets are held in place by face plate 234. The face plate 234 also includes window 132. In the illustrated embodiment, the face plate has a hole smaller than the magnet so that the magnet does not fall out. In some embodiments, the magnets 238 have a lip that is larger than the hole, but a face that fits through the hold to make better contact with the viewing platform 160. The magnets hold the sample holder 200 in place when the holder is placed on the viewing platform 160 of stage 150. In the illustrated embodiment, the viewing platform 260 on stage 250 is made of a magnetic material to exert more attractive force on the magnets 238 in sample holder 200. The stage 250 includes thumbscrews 166, as described above for adjusting tip and tilt of the platform 260.

Figure 2B:
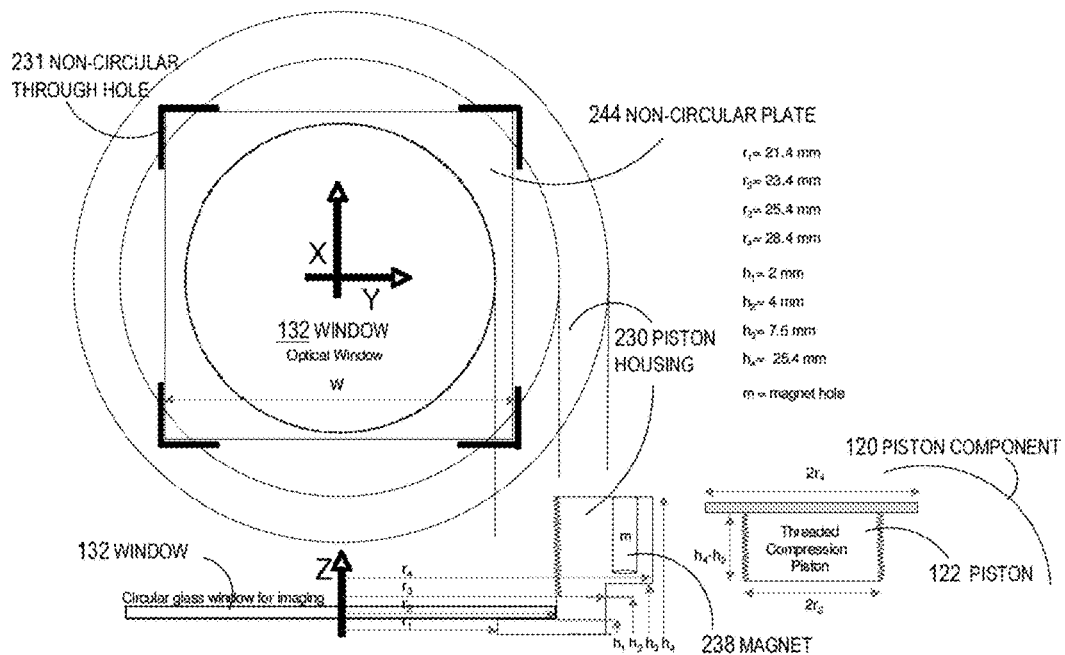
FIG. 2B is a diagram illustrating example dimensions of a piston housing and piston, according to an embodiment.

FIG. 2B is a diagram illustrating example dimensions of a piston housing 230 and piston component 120, according to an embodiment. This embodiment was fabricated to magnetically couple into a stage configured as the commercially available THORLAB™ of Newton, N.J. KM200 stage, but made of magnetic material. The through hole has threads at a radius $r_2$=23.4 millimeters (mm, 1 mm=$10^{-3}$ meters) that matches the radius of the threaded compression piston 122, which has a diameter of $2r_2$. The threads in the through hole start at a height $h_2$=4 min above the lower face of the piston housing 230. The circular glass covering the optical window 132 also has a radius of $r_2$=23.4 mm, and is set above a lower face of the piston housing 230 by a distance of $h_1$=2 mm, which has a circular opening of radius $r_1$=21.4 mm. The magnet hole for magnet 238 is in the piston housing 230 at a radius $r_3$=25.4 mm and the bottom of the piston housing 230 at this radius is at a height of $h_3$=7.6 mm and extends further to a radius of $r_4$=28.4 mm. The top of the piston housing 230 is at a height $h_4$=25.4 mm. The height of the threads on the piston 122 is $h_4-h_2$=21.4 mm.

FIG. 16A is a block diagram that illustrates an adjustable stage 1650 and removable sample holder 1610, according to another embodiment 1600. Sample holder 1610 includes a piston component 1620 and a piston housing 1630. The piston component 1620 includes threaded piston 1622 disposed in a threaded through hole. Piston component 1620 is attached to the piston housing 1630 after a sample is placed inside, using fasteners, such as clips or screws, indicated by arrows 1628.

The piston housing 1630 includes a through hole. In the through hole is placed a glass slide 1632 as window, a sample 1619, Agarose gel 1640 and plate 1644, such as another glass slide. The piston 1622 travels through the through hole to compress the sample 1619 against the window 1632 for viewing. The gel disk 1640 is included in the through hole between the sample 1619 and the plate 1644 to help fix the sample 1619 against the window to avoid lateral movement and to cushion the sample 1619 from the piston 1622 and plate 1644. The plate 1644 is included to prevent twisting motion of the threaded piston 1622 from distorting the gel 1640 and sample 1619. When the piston 1622 is inserted in the through hole of housing 1632, a surface of the sample is pressed flat against the top surface of the window 1632. The piston housing 1632 includes magnets 1638 to provide an attractive force to stage 1650, as indicated by dotted arrows. In the illustrated embodiment, the magnets 1638 are disposed in well holes formed in a base of piston housing 1630 where they are fixed using any manner known in the art, including relying only on the force of gravity and their own magnetic attraction to the stage 1650 below.

Stage 1650 includes a viewing platform 1660 with a viewing hole 1662 and a platform mounting 1652. In the illustrated embodiment the platform mounting 1652 is a X-Y-Z stage, from LUCID, INC.™, Rochester, N.Y., which can be stepped in small increments in all three spatial dimensions. Also in this illustrated embodiment, the platform 1660 is attached to platform mounting 1652 via a ball joint 1668 of fixed height and only two set screws 1666a and 1666b that are automated with micro-positioning actuators.

Figure 16B:
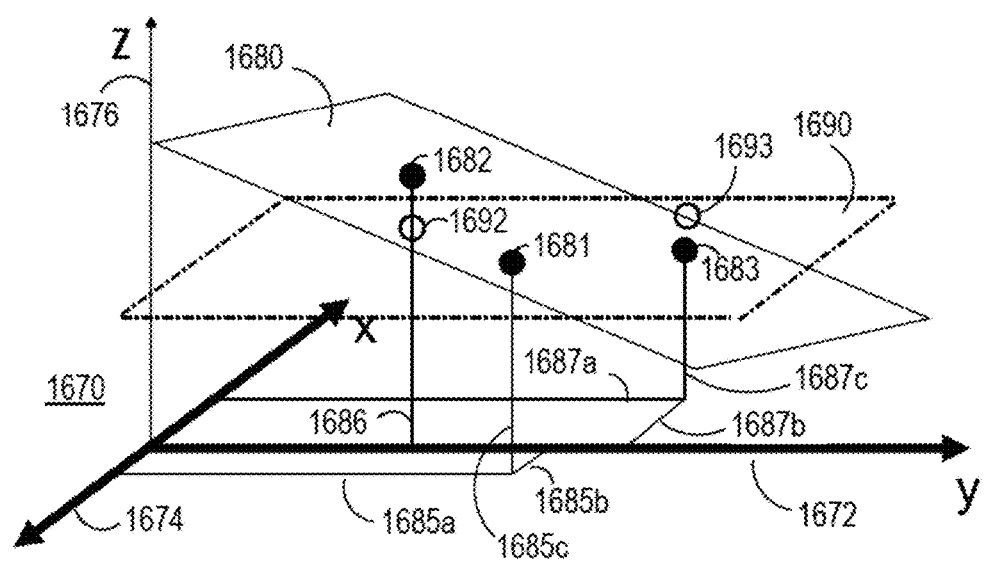
FIG. 16B is a block diagram that illustrates an automated adjustment according to an embodiment.

FIG. 16B is a block diagram 1670 that illustrates an automated adjustment according to an embodiment. The horizontal axis 1672 indicates distance in a y direction in arbitrary units; and the horizontal axis 1674 indicates distance in a perpendicular x direction in arbitrary units. The vertical axis 1676 indicates distance in a perpendicular, vertical z direction in arbitrary units.

According to this automated adjustment process, z-scans are acquired at three locations indicated by x-y coordinates below three pointes 1681, 1682, 1683 represented by solid circles, in a tilted plane 1680. It is desired to move these points to corresponding points 1681, 1692 and 1693, respectively, (the latter two represented by open circles) in a focal plane 1690 of the microscope.

The z-scan measures the position of the peak reflection intensity. The maximum intensity of the signal is always at the location of the glass interface with the tissue. The sample is moved axially at a particular x-y location (e.g., at y distance 1685a and x distance 1685b for point 1681) to determine an axial position (e.g., 1685c) with maximum intensity. The three axial signal peak positions (e.g., 1685c, 1686 and 1687c), at the corresponding x-y positions are determined to deduce the tilt of plane 1680 relative to the focal plane 1690. The relative adjustments of the two automated set screws 1666a and 1666b are determined to move point 1682 in the tilted plane 1680 down to point 1692 in the focal plane 1690, and point 1683 in the tilted plane 1680 up to point 1693 in the focal plane 1690.

In some embodiments, in addition to, or instead of, automating the adjustment of the viewing platform 1660, the tilt of plane 1680 relative to the desired focal plane is determined once, and for subsequent measurements, as the objective lens is stepped horizontally, the vertical position of the objective lens is corrected by the automated vertical (z direction) movement of the objective lens through the hole 1662 based on the tilt of the plane 1680. Vertically stepped objective lenses for confocal microscopy are commercially available.

3. Image Merging for Mosaic

The quality of mosaics in confocal imaging over a large area is critical to diagnosis of tumors in cancer pathology. Previous work led to a stitching algorithm that cropped individual images and stitched them together in a constant fashion across the face of the mosaic. The image acquisition hardware moved the sample a fixed distance between acquiring images. The fixed distance was less than the image width so that there was some overlap which was later cropped away. Data processing involved a priori knowledge of the exact amount of overlap which was assumed to be identical between neighboring frames everywhere within the mosaic.

A new technique was developed to tailor fit each frame into the mosaic. Thus, in some embodiments, a method for merging overlapping images from a confocal microscope includes determining a translation of a first image with respect to a second image that minimizes a difference of light intensity in an overlapping region between the first image and the second image. Light intensities from one pixel in the overlapped region of the first image and a corresponding pixel in the translated second image are averaged to produce a merged image.

In a particular embodiment, images are set to overlay with an initial guess at the offset, which is input by the user. In embodiments with a priori knowledge, the initial guess is set equal to the a priori approximate overlap based on the step size and image size. For example, in the case of the stepping confocal microscope, the general positioning of adjacent frames is known. Typically there are about 20 overlapping pixels horizontally and 10 overlapping pixels vertically but these parameters can vary due to mechanical non-uniformities during acquisition of the two dimensional array of individual images. The tailor-fitting process iteratively guesses at the offset until the correct offset (relative positioning) for the two images is determined where the intensity difference between pixels in the overlapping region is a minimum. The process works to minimize the error which consists of the sum of the overlapping pixel differences normalized by the number of overlapping pixels. In this manner, the mean pixel error is determined and minimized such that the same features in the two images are co-localized. In some embodiments, images in a strip are translated one at a time to construct an entire strip. When all such strips are formed, each strip is translated, one at a time to the already translated strips to form the mosaic.

In some embodiments, 3-D image cubes are merged, first by merging cubes in one dimension into strips of cubes, for each of several depths, as described above for images. All the strips of cubes merged at one depth make what is called herein a panel. When all such panels are formed, each panel is translated, one at a time to the already translated panels to form the mosaic cube. This embodiment is useful in sets of slices from scanning devices such as X-ray computed tomography and magnetic resonance (MR) imagery, for example, for in vivo melanoma detection. In some embodiments, this process is extended to fourth and higher dimensions, e.g., to include a temporal dimension.

Figure 3A:
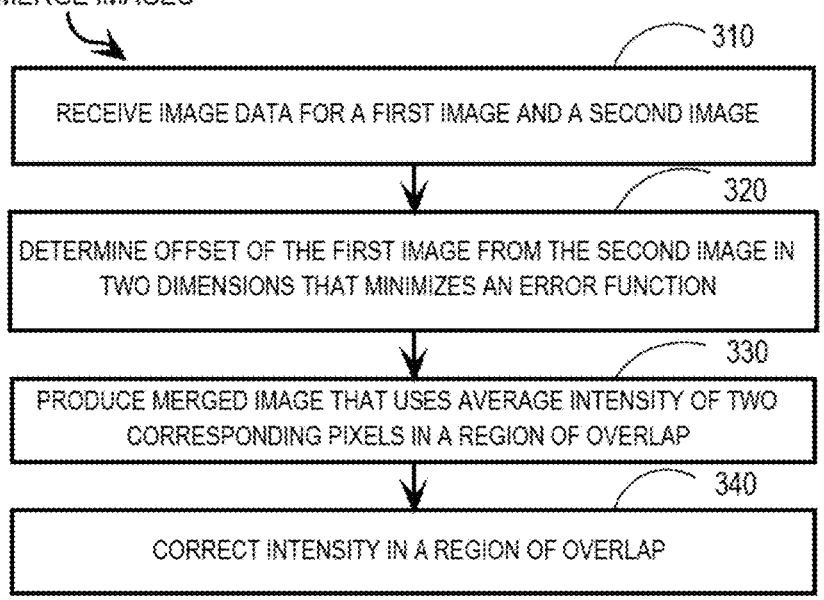
FIG. 3A is a flow diagram that illustrates at a high level a method to produce a merged image, according to an embodiment.

FIG. 3A is a flow diagram that illustrates at a high level, a method 300 to produce a merged image, according to an embodiment. Although steps are shown in FIG. 3 and subsequent flow diagrams in a particular order for purposes of illustration, in other embodiments one or more steps or portions thereof are performed in a different order or overlapping in time or are omitted or additional steps are added, or the method is changed in some combination of ways.

In step 310, image data is received for two or more overlapping images from a confocal microscope. In step 320, an offset is determined that minimizes an error, based on the average intensity difference between pixels at corresponding locations in an overlapping region. Any method may be used to determine the best offset. In one embodiment, a gradient search is performed in which a change in offset is associated with a change in error, and a new offset is selected in a direction that reduces the error. In step 330, the intensities at two or more pixels at a corresponding location are averaged to form a merged image, also called a mosaic. In step 340, intensity in an overlap region is corrected for non-uniform illumination. In some embodiments, step 340 is omitted; and, in some embodiments, an illumination correction described in the next section is employed.

Figure 3B:
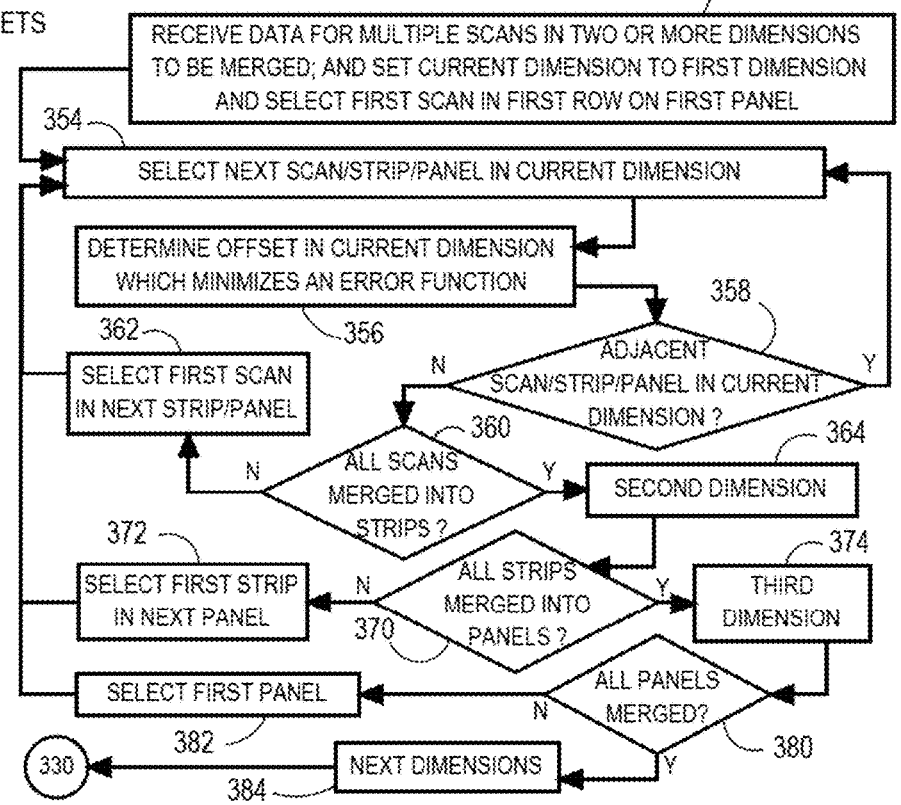
FIG. 3B is a flow diagram that illustrates a step of the method of FIG. 3A, according to an embodiment.

FIG. 3B is a flow diagram that illustrates a step of the method of FIG. 3, according to an embodiment. Method 350 depicted in FIG. 3B is a particular embodiment of step 310 and step 320 for determining multidimensional offsets. In an illustrated embodiment of step 310 and 320, method 350 is applied in two dimensions to produce a single panel that is a mosaic of individual small images.

In step 352 of method 350, all the scan data to be merged is received. As used herein a scan is a multidimensional array of intensity values, such as a 2-D image of pixel elements (pixels), a 3-D volume of volume elements (voxels), or a higher dimensional array of scan elements. As used herein a scan element refers to an individual pixel, voxel or other higher dimensional array element of a scan. In step 352, a first scan for a first strip in a first dimension for a first panel (for a first time or other one or more dimension) is selected to start the process. In the illustrated embodiment, a first individual image in a first strip of images for the x direction for a first mosaic is selected during step 352.

In step 354, the next adjacent scan or strip or panel in a current dimension is selected. For example, the next adjacent image in the x dimension is selected. In step 356 an offset is determined in the current dimension to minimize an error function. In the illustrated embodiment, the error function is based on differences in intensities between corresponding scan elements in an overlapping region between the next scan (or strip or panel, designated scan/strip/panel) and the last scan/strip/panel already translated. For example, an offset in the x-dimension is determined for the adjacent image.

In step 358 it is determined whether there is an adjacent scan/strip/panel still to be offset. If so, control passes back to step 354 to select it as the next one. For example, if there is still another image adjacent to the first strip in the x dimension, then it is the next image for which an offset is determined.

If it is determined in step 358 that there is not an adjacent scan/strip/panel then the current strip or panel or cube to be offset is complete. Control passes to step 360. For example, when the last image in the first strip is offset, there is no adjacent image in the x dimension and control passes to step 360.

In step 360 it is determined whether all scans are offset into strips. If so, then the first dimension is finished and control passes to step 364 to set the current dimension to the second dimension. In some embodiments, step 360 includes determining whether the current dimension has already been set to a higher dimension.

If it is determined in step 360 that all scans have not been offset into strips, then control passes to step 362 to select the first scan in the next strip. If several panels (or times) are being offset, then the first scan in the next strip may be in a different panel (or different time). Control then passes back to step 354 to select the next adjacent scan.

After step 364, control passes to step 370. In step 370 it is determined whether all strips are offset into panels. If so, then the second dimension is finished and control passes to step 374 to set the current dimension to the third dimension. If there is no third dimension (e.g., when determining two dimensional offsets for individual images in a mosaic, there is no third dimension), then the offset determination is complete. In this embodiment, steps 374, 380, 382 and 384 are omitted so that control passes directly to step 330 in FIG. 3A. In some embodiments, step 370 includes determining whether the current dimension has already been set to the third or higher dimension.

If it is determined in step 370 that all strips have not been offset into panels, then control passes to step 372 to select the first strip in the next panel, such as the first strip in the first panel. If several panels (or times) are being offset, then the first strip in the next panel may be in a different panel (or different time). Control then passes back to step 354 to select the next adjacent strip.

After step 374, control passes to step 380. In step 380 it is determined whether all panels are offset. If so, then the third dimension is finished and control passes to step 384 to continue the process for a fourth and higher dimensions, if any. In some embodiments, step 380 includes determining whether the current dimension has already been set to the higher dimensions.

If it is determined in step 380 that all panels have not been offset, then control passes to step 382 to select the first panel. If several cubes are being offset, then the first panel may be in a different cube (e.g. at a different time). Control then passes back to step 354 to select the next adjacent panel. The process continues in step 384 until offsets for all multidimensional scans in all dimensions have been determined. Then control passes on to step 330 in FIG. 3A.

FIG. 4A, FIG. 4B, FIG. 4C, FIG. 4D and FIG. 4E are adjacent images that illustrate the application of image merging for the confocal microscope, according to an embodiment.

Figure 4A:
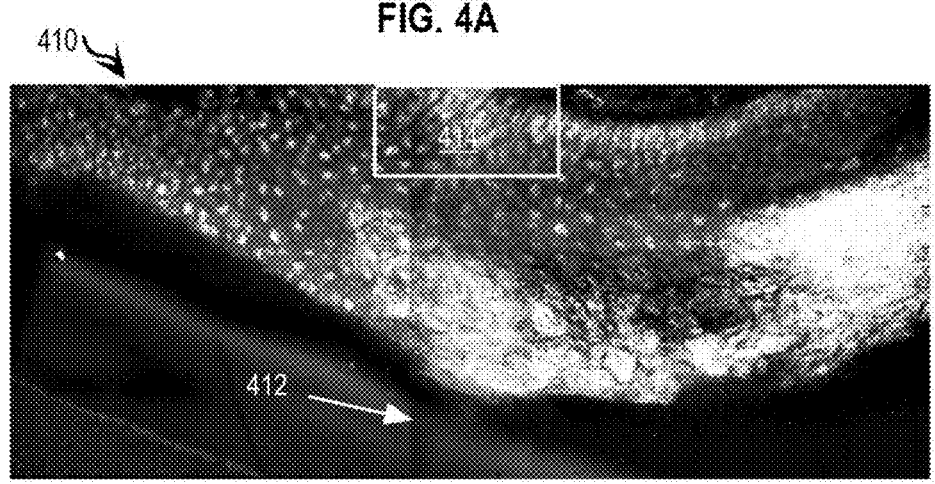
FIG. 4A, FIG. 4B, FIG. 4C, FIG. 4D and FIG. 4E are fluorescence images that illustrate the application of image merging for the confocal microscope, according to an embodiment.

FIG. 4A through FIG. 4D shows the second step in stitching two adjacent images together, step 320 above, which is the alignment of the images to superimpose with proper feature co-registration, and the third step, step 330, of averaging the intensities at pixels in the overlapping region. FIG. 4A is an image 410 that illustrates an initial guess at the relative position. Image misalignment is evident at a dark line 412. Inset box indicates a portion 414 of image 410 that is shown in greater detail in a subsequent figure.

Figure 4B:
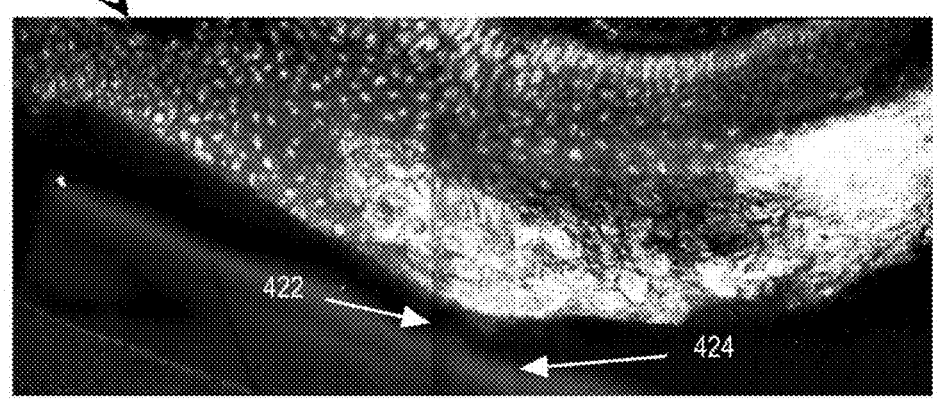
Figure 4C:
Figure 4D:

After minimizing the error in step 320, a comparison of the two images is shown in FIG. 4B. FIG. 4C shows a magnified view of the portion 414 indicated by the insert box in FIG. 4A after averaging intensities in pixels at corresponding locations. Because this image portion is obtained before the best offset is determined, the two images are misaligned, blurring the cells in the overlapping region where the images are averaged. FIG. 4D shows the portion 444 of an image at the same location as portion 414 of the merged image, but after translation by the offset that minimizes the error. The cells are no longer blurred after the program is run because they have been spatially matched.

While feature alignment is better, intensity discontinuities remain. FIG. 4B shows an interim composite image 420 that has a vertical dark band in the center with a left edge 422 of intensity discontinuity where the band borders the left image, and a right edge 424 of intensity discontinuity where the band borders the right image. The dark band is composed of the edges of two individual images that, due to vignetting of the optical microscope, are darker than the centers of the individual images. Vignetting is the process of scanning the measurement spot along a focal plane of the objective lens by varying the angle of incidence of the illuminating light beam at the objective lens. While the angled beam hits the target sample at a different spot, a portion of the parallel illuminating beam is lost outside the lens. Thus the outer pixels in each individual image are less illuminated than the central pixels.

Figure 4E:
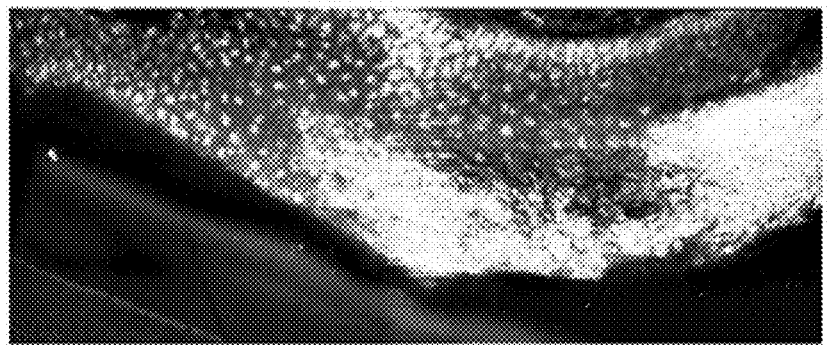

Since it is challenging to fully optimize the microscope for uniform field sensitivity, intensities in the overlapping region were normalized to the rest of the image, in some embodiments, in step 340. Pixels ($P_{ll}$) to the left of the left edge 422 have a higher value than pixels ($P_{lr}$) to the right of the left edge 422. For each horizontal row of pixels within the band, a multiplier (m1) was found, such that $P_{lr}*m1=P_{ll}$. Similarly, a second multiplier (m2) was found such that $P_{rl}*m1=P_{rr}$. A linear vector that varied from m1 to m2 was multiplied by each horizontal row to achieve normalization of the row such that it transitioned continuously from the left image to the right image. In this manner, the dark band in the center of the merged image 420 was removed. The result is shown in FIG. 4E as image 450.

4. Illumination Correction

In another set of embodiments, a method for correcting illumination includes receiving a set of multiple images from a confocal microscope. Each image includes a two dimensional array of pixels located by a row number and a column number; and each image covers a different portion of a single sample. A pixel average intensity is determined for each pixel location by averaging intensity values at the pixel location over every image of the set. A pixel illumination correction based on the pixel average intensity for each pixel location is applied to every pixel at the pixel location in each image in the set of images.

Figure 5:
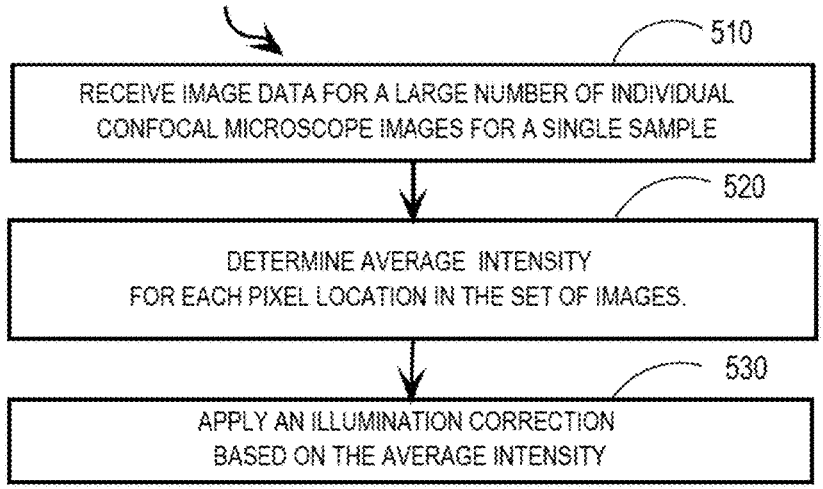
FIG. 5 is a flow diagram that illustrates at a high level a method to correct intensity for non-uniform illumination, according to an embodiment.

FIG. 5 is a flow diagram that illustrates at a high level a method 500 to correct intensity for non-uniform illumination (also called illumination correction herein), according to this embodiment. In step 510, data for a large number of individual images is obtained. For example, in some embodiments, all the individual images (430×430 μm) for a wide field of view (12×12 mm) mosaic are received. This is about 30×30 images for 10% overlap, e.g., about 1000 images. In step 520, the average intensity at each pixel location is determined. For example, at about 0.5 μm resolution, each image has one million pixels, so one million values, each averaged over 1000 individual intensity values, are obtained.

In step 530 an illumination correction is applied to each pixel based on the average value for the location of that pixel. In some embodiments, the correction is determined by multiplying the pixel in each image by a ratio of a peak pixel intensity in the average image to the pixel in the corresponding location in the average image.

5. Fast Staining for Nuclear Fluorescence Contrast

In another set of embodiments, a method for detecting cell nuclei with a confocal microscope includes contacting a surface of a sample of excised tissue with a 1 milliMolar (mM, 1 mM=$10^{-3}$ Molar) solution of acridine orange for 20 seconds. A spot on the surface of the excised sample is illuminated with a laser beam of wavelength about 488 nanometers (nm, 1 nm=$10^{-9}$ meters). Fluorescent emission intensity from the spot is detected in a wavelength range above about 500 nm. Because the stain is accomplished so quickly, fluorescent confocal images with good nuclear contrast can be achieved rapidly compared to histology sections.

Figure 7B:
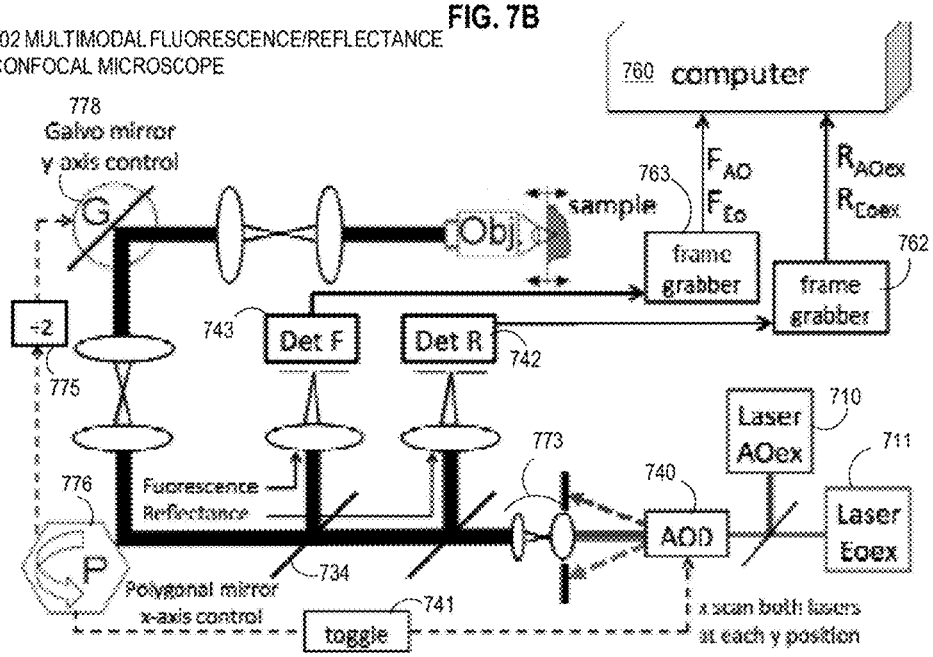
FIG. 7B is a block diagram that illustrates a multi modal reflectance/fluorescence confocal microscope, according to another embodiment.

FIG. 6 is a flow diagram that illustrates at a high level a method 600 for obtaining fluorescence that provides high contrast to cell nuclei with a fast stain, according to an embodiment. In step 610 the surface of a sample is contacted with a 1 milliMolar (mM, 1 mM=$10^{-3}$ Molar) solution of acridine orange for 20 seconds. In step 620, one or more spots on a surface of a sample are illuminated with laser light having a wavelength about 488 nanometers (nm, 1 nm=$10^{-9}$ meters). In some embodiments, a confocal microscope light source is swapped out, e.g., a 830 nm laser is replaced by a 488 nm laser during step 620. In step 630, fluorescent emission (also called fluorescence emission intensity), e.g., at wavelengths of about 500 nm and above, is detected at the spot. An apparatus for detecting this fluorescent emission simultaneously with a reflectance emission intensity is depicted in FIG. 7A, with alternative embodiments depicted in FIG. 7B and FIG. 7C. In step 640, the presence of cell nucleus at the spot is determined based on the fluorescent emission detected.

As described in Gareau, a nucleus in a basal carcinoma cell (BCC) tumor is typically seen as about 100 pixels in an individual image but subsequently appears as only about 1 pixel in a mosaic. This is due to scaling down of full-resolution mosaics by about a factor of 10 to match the pixel size and resolution to that of a 2x-view of histology. Using a Mie-scattering model for detectability in a reflectance confocal microscope, the nuclear contrast was calculated to drop from about 100 to about 1 relative to the surrounding bright dermis, resulting in a significant loss of visual detectability of small and tiny BCC tumors.

In fluorescence, however, with a contrast agent that specifically stains nuclei, very little light may be collected from the surrounding dermis (except, perhaps, for weak autofluorescence). Detection of both large and small BCC tumors and also squamous cell carcinomas (SCCs) in fluorescence with methylene blue and toluidine blue was recently reported. We chose acridine orange which is another well-proven nuclear stain for confocal microscopy. Acridine orange differentially stains nuclear DNA and cytoplasmic RNA in endothelial cells. However, staining was expected to be only of the nucleus in epidermal keratinocytes. Acridine orange has a quantum yield of 75% when bound to DNA and extinction coefficient of about 53,000 Moles per liter-centimeter (ltr-cm). Using an analytical model for detectability in a fluorescence confocal microscope, the nuclear contrast was estimated to drop from $10^5$ to $10^3$ relative to a significantly darkened dermis. Thus, small and tiny tumors were expected to be seen in mosaics.

Here, the use of fluorescence with acridine orange was shown to increase the nuclei-to-dermis contrast of BCC tumors in confocal mosaics. The visual comparison of mosaics to the corresponding Mohs frozen histology was favorable. The results show that the detectability of small BCC tumors such as micronodular, infiltrative and sclerosing was considerably improved over that in reflectance alone. The detectability of both large and small tumors demonstrates the feasibility of large area-confocal mosaicing microscopy toward rapid pathology in surgically excised tissue to potentially expedite and guide surgery.

Only the excised tissue surface is examined in Mohs histology, to determine the lateral extent of tumor. Thus, for imaging, staining with acridine orange need not surpass a few cell layers. A cell layer in skin is about 10 microns (μm)

thin; and the Mohs surgeon usually examines 3 to 5 frozen histology section, each being about 5 to 6 μm thin. Hence, it was considered to image to a maximum depth of about 30 μm which corresponds to about 3 cell layers. (This depth is also approximately the maximum to which real-time confocal imaging is possible in dermal tissue with very low milliwatt-power blue 488 nm-illumination.) Using a diffusion distance of 30 μm, the average diffusion time is 0.6 milliseconds for tumor and 0.37 seconds for normal tissue.

FIG. 7A is a block diagram that illustrates a multi modal reflectance/fluorescence confocal microscope 700, according to an embodiment. This microscope is capable of detecting the fluorescence emission intensity described in step 630, above; as well as multimodal measurements described in more detail in the next section.

Confocal microscope 700 includes components present in an externally supplied reflectance confocal microscope, such as lenses 770, mirrors 772, 7X beam expander 773, relay telescopes 774, rotating polygon 776 to sweep through the scanning angles of the illumination and returned beams in one dimension (x), galvonometric scan mirror 778 to change scan angle in a perpendicular dimension (y), objective lens 780, polarizing beam splitter 724, and avalanche photodiode ($APD_R$) 722 for detecting reflectance emission intensity in a reflectance beam 720.

The confocal microscope 700 includes new components, enclosed in ovals, such as new stage and sample holder 790 (e.g., as depicted in FIG. 1 or FIG. 2A and FIG. 2B). Confocal microscope 700 also includes an Argon-ion laser 710 emitting in a wavelength range that includes 488 nm, and a 488 nm selection filter 714. The laser 710 replaces the externally supplied original laser emitting at 830 nm in order to excite fluorescence in the acridine orange dye introduced into the sample. The illumination of tissue is with low-level power of 0.3 to 1 milliWatts (mW, 1 mW=$10^{-3}$ Watts). Also added to microscope 700 is a dichroic beamsplitter 734 to reflect only the fluorescence beam 730 into a new fluorescent channel. The fluorescent channel includes a 488 nm rejection filter 735, lens 736 and avalanche photodiode ($APD_F$) 738 for detecting fluorescence emission intensity in the fluorescence beam 730.

In an experimental embodiment used to generate some images described hereinafter, not all the improvements described above were included. In this experimental embodiment, the fluorescence detection optics consists of a CHROMA™ of Rockingham, Vt., 510DCSPRX dichroic beamsplitter, an OMEGA OPTICAL™ of Brattleboro, Vt., 510EFLP excitation rejection filter to block extraneous reflected light and a PERKIN-ELMER™, of Vaudreuil, Quebec Canada, C30659-900-R8A avalanche photodiode. Detection in the fluorescence channel was mainly of the emission from the acridine orange-stained nuclei with almost none from the cytoplasm. Autofluorescence from the dermis is a few orders of magnitude weaker than the fluorescence from acridine orange and hence was not detected for the low illumination power and tightly confocal (i. e., small pinhole) detection conditions.

A custom-designed water immersion objective lens (StableView, of LUCID INC.™) was used for imaging through a 1 mm-thick glass slide. Instead of thin cover-slips that are conventionally used with objective lenses, a thick glass slide was used for mounting and stabilizing unconventional tissue specimens such as surgical excisions. The objective lens features 30× magnification to provide a 430 μm field-of-view. With a numerical aperture of 0.9, the calculated axial section thickness is: $\Delta z=1.4n\lambda/NA^2=1.1$ μm and lateral resolution is: $\Delta x=0.46\lambda/NA=0.25$ μm, which is adequate for imaging nuclear morphology. A water-based gel was often substituted for water as an immersion medium.

Surgical excisions are often thick, large and of unusual shape. Furthermore, the tissue is fresh, living, hydrated, mechanically compliant and hence not easy to mount in a microscope. A custom tissue fixture, as described above, was engineered for Mohs surgical excisions to be mounted and gently compressed onto a microscope slide. The embodiment that produced the images below used a threaded piston to be tightened for gently compressing and embedding an excision in a gel disk, so as to stabilize the excision. Distortion from the rotational motion of the piston that would cause the gel and subsequently the edges of the tissue to twist and distort is prevented as described here or above. For the example embodiment used to generate the images described below, a thin polycarbonate disk and needle-roller bearings obtained as part number 5909K31 from MCMASTER-CARR™ of New Jersey, was placed between the piston and the gel disk. The fixture allows repeatable and accurate control of the flattening, tip, tilt, sag and stability of the tissue surface to be imaged. The functionality of the tissue fixture mimics the operation of a cryostat which is the standard equipment for preparing frozen histology sections for Mohs surgery. Imaging in reflectance was used to guide z-distance and tip and tilt adjustments such that the tissue surface was oriented exactly parallel to the focal plane of the objective lens. The process involved translating the mounted excision laterally and adjusting four thumbscrews until the focus moved along the reflective water/tissue interface. This alignment enabled acquisition of images contiguously over large areas of 10 to 20 mm.

After the excision was mounted in the tissue fixture and properly positioned and oriented, confocal images were acquired. Images were acquired of the surface of the excision. Because of the thawing, staining and rinsing process, small distortions in the imaged surface were expected due to the compliance of the tissue. Thus, the mosaics were expected to show a close but not an exactly one-to-one correspondence to the frozen sections that were prepared by Mohs technician during surgery.

Of the 3 to 5 frozen histology sections that are prepared during surgery, the Mohs surgeon usually examines the first to determine the lateral spread of the tumors on the excised surface. Occasionally, if the quality of the first section is poor, or, if the determination of tumor margins is not very clear, the Mohs surgeon examine the remaining sections. Additional sections are sometimes prepared if the Mohs surgeon desires to further examine deeper layers of tissue. For the example images shown below, however, images were acquired and mosaics created only of the exposed surface of the discarded excisions. This exposed surface corresponds to the last Mohs frozen section. Subsequent comparison of the mosaics to histology was therefore limited to the last frozen section.

Confocal mosaics can be quickly acquired. For acquisition, a continuous step-and-capture routine requires about 5 minutes for 36×36 images. Transferring and archiving images followed by processing to create a mosaic requires another 4 minutes on another PC. Thus, total time to create a mosaic is up to 9 minutes for the embodiment that produced the images below. Faster times are expected for other embodiments that incorporate other features described above.

At the edges of images, dark bands due to field curvature-induced artifact and illumination fall-off due to vignetting were noticeably seen. These were corrected for in the image-stitching algorithm, based on calibration measurements in the confocal microscope for the images shown below. The Petzval field curvature in the microscope was calculated to be about 3.8 μm and measured to be about 5 μm. When focused at the surface of the excision, field curvature results in tissue being seen in the center but surrounded with an annular ring at the periphery in the image. The ring is due to the overlying glass window in the experimental embodiment and results in an illumination artifact. The artifact appears as bright bands in reflectance but dark bands in fluorescence. By focusing slightly deeper than 5 μm beneath the tissue surface, the artifact was often minimized. As a result of deeper focusing, small mismatches to the frozen section of the surface and small losses in correlation to frozen histology were anticipated. The dark bands were largely eliminated by cropping the 10%-overlap between images in the image stitching algorithm of the experimental embodiment.

To characterize vignetting in the experimental embodiment, the illumination fall-off across the field-of-view was measured with a standard fluorescent target. A drop of acridine orange was compressed between a microscope slide and cover slip and an axial stack of images was acquired. The images were averaged in depth to determine the vignetting in both x- and y-directions. The vignetting was corrected for with an inverted-brightness polynomial fit in the image-stitching algorithm.

The translation of the linear XY stages was set parallel to the x- and y-directions of the optical raster scan in the confocal microscope. Mosaics of a reflective grating test target were used to calibrate for angular misalignments. Gareau shows a mosaic of a reflective grating target (Ronchi ruling with 200 lpi from EDMUND INDUSTRIAL OPTICS™ of Barrington, N.J.) that demonstrates angular alignment and lateral registration in both x- and y-directions. The mosaic was created by cropping 10%-overlap between images and stitching 3×3 images. The grating lines appear continuous to within 5 pixels between images. However, as explained below, full-sized mosaics are scaled down by 8 to 10× such that the lateral mismatch is within sub-pixel and not noticeable in the final display.

Mosaics in the experimental embodiment were created with MATLAB™ software (version 7.4, MATHWORKS™, Natick, Mass.). The algorithm implemented the following steps: cropping of the overlap between images, merging of images into a single composite mosaic and correction for the residual dark bands between images. The amount of cropping was 10% as predefined by the stepping distance of the XY-translation stages during the image acquisition, and further precisely adjusted by measurements of overlap using image analysis software (IPLab Spectrum, version 3.6.5, BD BIOSCIENCES, INC.™, Rockville, Md.). Based on experience, the overlap between images remained repeatedly consistent across large mosaics with minimal errors. After cropping, the images were concatenated into a single composite mosaic. The cropping removes the dark bands due to field curvature. The illumination fall-off due to vignetting was then corrected for with an inverted-brightness correction polynomial fits in both x- and y-directions. The polynomials were empirically designed to flatten the illumination fall-off across images. The design of the polynomials is specific to these fluorescence mosaics but is based on a de-stripe filter that was originally authored by Marc Lehman, and is available as open-source software called GNU Image Manipulation Program (GIMP). Lehman's executable and source code may be downloaded from the Internet.

The pixel grayscale or brightness is defined as I(x, y), where x and y are column and row positions, respectively, of individual pixels. Horizontally across the entire mosaic, the mean brightness profile I(x) was determined by averaging pixel values in columns as a function of x-pixel location. Similarly, vertically across the entire mosaic, the mean brightness profile I(y) was determined by averaging pixel values in each row as a function of y-pixel location. Averaging across columns and rows of the entire mosaics provides a globally smoothed low frequency estimate of the spatial high-frequency variations in fluorescence from the tissue. The mean brightness profiles represent both the fluorescence signal from the central regions of the images and the illumination fall-off at the edges. Polynomial fits for brightness in x-direction and y-direction were further modeled in terms of a rolling average of the mean brightness profiles.

The rolling average-based polynomial fits are locally smoothed versions of the mean brightness profiles. The rolling average polynomial fits also represent both the fluorescence signals from the central regions and the illumination fall-off near the edges of the images. The purpose of these polynomial fits was to spatially isolate the regions of low-frequency illumination fall-off near the edges of the images from the relatively high-frequency fluorescence signals in the central regions. Isolating the two regions subsequently allowed corrections to be applied mainly to the illumination fall-off but none to the fluorescence signals. The width of the filter, W, was empirically tested in the range of 24 to 100 pixels. On the basis of visual examination, a small width of 36 pixels was found to provide the optimum match of the rolling average polynomial fit to the mean brightness profile. Smaller windows produced too little smoothing of the differences between the spatially high-frequency fluorescence signals in the central regions of the images and the relatively low-frequency illumination fall-off near the edges, and therefore undesirable isolation of the two regions. This resulted in minimal corrections to fluorescence signal but too little correction for illumination fall-off. Larger windows resulted in too much smoothing and, again, undesirable little isolation, which resulted in too much correction of illumination fall-off and also unwanted large corrections to the fluorescence signal.

Subtracting the mean brightness profiles from rolling average polynomial fits substantially removed the fluorescence signals from the central regions and mainly represented the illumination fall-off near the edges. This subtraction resulted in an inverted-brightness correction polynomial. The correction polynomials were minimal in the central regions of images of the mosaic which are relatively uniformly illuminated. Visual examination showed that, with the rolling average filter width of 36 pixels, the correction polynomials were close to zero. However, they were appropriately large near the edges that display illumination fall-off. Thus, the correction polynomials were applied mainly in the regions of illumination fall-off but not in the central regions of images in the experimental embodiment.

In the experimental embodiment, the inverted-brightness correction polynomials were added back to the original mosaic to flatten the illumination fall-off across the images. The illumination fall-off at the edges between images were corrected in the y-direction (row by row) and in the x-direction (column by column) to produce a new brightness or pixel grayscale distribution.

Since the corrections for the experimental embodiment are based on a rolling average approximation of the actual pixel brightness distribution, a scaling factor was used to adjust the brightness in the regions of fluorescence signal and vignetting to appropriate levels. The scaling factor was empirically tested in the range of 8 to 128. On the basis of visual examination, a factor of 32 was determined to provide the optimum brightness for the mosaics. Smaller scaling factors resulted in mosaics appearing dark; whereas larger scaling factor resulted in too much brightness and saturation. To every row (or column) of pixel grayscales I(x, y), the inverted-brightness polynomial fits were applied proportionally to the locally averaged fluorescence signal. This approach minimized the corrections in relatively uniformly illuminated central regions of images and limited corrections mainly to the illumination fall-off near the edges.

The algorithm for the experimental embodiment worked effectively to correct the well-defined loss of illumination at the edges of images due to vignetting. The algorithm was applied to the fifty mosaics that were acquired to achieve repeatable results. The advantage of this algorithm is that the correction polynomials may be determined in a "blinded" manner to any given mosaic without requiring a priori knowledge of vignetting in the microscope. The mean brightness profiles and rolling average polynomial fits produced an estimate of the illumination fall-off due to vignetting. Any additional instrumental errors in illumination were also estimated and corrected for. The main step is that values for width W and scaling factor were initially determined in 2 to 3 mosaics. We have found the values may be consistently used afterwards. The corrections were close to zero in the fluorescence signal such that visual gain or loss of contrast appeared to be minimal and did not appear to affect subsequent analysis of mosaics and comparison to histology. The final processed mosaic was saved in TIFF format.

Each image consisted of 640×480 pixels, was 8-bit grayscale and consumed about ¼ megabytes (MB, 1 MB=$10^6$ bytes of eight binary digits) of memory. Thus, a full mosaic of up to 36×36 images consists of 23,040×17,280 pixels and consumes 325 MB of memory. The mosaics were scaled down using bilinear interpolation to make the displayed lateral resolution and pixelation equivalent to that of a 2×-magnified view of histology. The final mosaic is displayed to the Mohs surgeon with lateral resolution of about 4 mm, and consisted of about 2500×2500 pixels and consumed less than 4 MB of memory. Mohs excisions are sometimes oval or elongated in shape and may be as long as 30 mm. For such excisions, larger mosaics displaying up to 30×10 mm were created by acquiring multiple adjacent 10×10 mm-mosaics and joining them in PHOTOSHOP™ from ADOBE SYSTEMS INCORPORATED™ of San Jose, Calif.

Mosaics were observed on a 30-inch flat-screen monitor (DELL™ 222-7175 with a GeForce 8800 GTS video card from DELL™ of Round Rock, Tex.) of 2,500×1600 pixels. A full-sized mosaic is equivalent to a 2×-magnified view. With digital zooming, smaller portions, called sub-mosaics, were also observed. The display of sub-mosaics is equivalent to higher magnifications of 4× and 10×.

Fifty mosaics were compared to the corresponding Mohs frozen histology sections. The frozen sections were those that were prepared during surgery for the Mohs surgeon. These sections were prepared with standard hematoxylin-and-eosin (H&E) stains. The imaged surface of the frozen, thawed, discarded excision corresponds to the final section that was prepared. Therefore, mosaics were compared to the last Mohs frozen section.

Nuclear and morphological features were evaluated in the mosaics and compared to the histology. The Mohs surgeon evaluated those features that are routinely examined in histology and are necessary to detect BCC tumors versus normal skin. The features for the presence of BCC tumors are nuclear pleomorphism (atypical shapes and sizes), increased overall nuclear density, palisading ("picket-fence" type arrangement of nuclei around the inner periphery of tumor), clefting (dark-appearing "moats" around the outer periphery of tumors that are filled with optically clear mucin) and the presence of inflammatory infiltrates. The features for normal skin are epidermal margin (epidermis along half the periphery of the excision), hair follicles, sebaceous glands and eccrine glands.

The Mohs surgeon uses an objective lens with 2× magnification to quickly examine large areas of histology. Objective lenses with 4× and 10× magnifications are used, when desired, for closer inspection of nuclear detail. Entire mosaics and sub-mosaics were evaluated at equivalent magnifications. The sub-mosaics usually consisted of a quarter of the entire mosaic, since the Mohs surgeon usually records the presence or absence of BCC tumor in quadrants.

Experiments were performed to investigate the effects of exposure for 20 seconds to 1 milliMoles (mM, 1 mM=$10^{-3}$ Moles) acridine orange on subsequent histology. Possible effects include tissue decay, degradation of RNA and DNA due to autolysis, room-temperature digestion of tissue due to proteolytic enzymes, swelling of cytoplasm and separation of the epidermis from the dermis. These effects may lead to prevention of H&E staining and a "washed out" appearance. Ten excisions were reprocessed for frozen H&E stained histology sections after acridine orange-staining and confocal imaging. The frozen sections were compared to the corresponding Mohs sections. The evaluation and comparison, performed under "blinded" conditions by the Mohs surgeon, analyzed possible tissue disruptions and distortions as well as the chromaticity of staining.

The fifty mosaics that were created, for comparison to histology, demonstrated repeatability of the tissue fixturing and mosaicing algorithm. Lateral registration between the edges of images was observed to be sub-pixel. The mosaics appeared reasonably seamless and contiguous with high resolution and reasonably uniform illumination over large areas of tissue, and were useful for clinical visualization and comparison to histology. The image quality of the mosaics was repeatable and consistently high for examination of morphologic features that are clinically important for surgical pathology. In Mohs skin excisions, the features include the edges of the tissue, epidermal margins, normal dermis, and nuclear detail and gross morphology of BCCs.

Excellent comparison between confocal mosaics and the corresponding Mohs frozen histology was achieved for BCCs as well as normal skin morphology. The epidermal margin of excisions along with the dermo-epidermal junction was clearly and repeatably identified on the mosaics. Normal structures in the dermis such as sebaceous glands, hair follicles, and eccrine glands were easily and consistently visualized. The gross morphology of BCCs in terms of shape, size and location of tumor nests as seen in the mosaics corresponded well to that seen in frozen histology. Additionally, the atypical morphology of nuclei in BCCs in terms of pleomorphism (varying shapes, sizes, orientations and irregular distributions), crowding (increased density), and palisading was clearly visualized in the mosaics and corresponded well to the histology. Inflammatory infiltrates were seen around BCC nests. Nuclear staining with acridine orange clearly provided enhanced fluorescence contrast of tumors over the background dermis for both large and small types of BCCs. The large types include superficial and nodular while the small types include micronodular, infiltrative and sclerosing. Since the large types were easily detectable (including with reflectance contrast), we present the more challenging cases of small types in the following figures.

The effect of acridine orange-staining and confocal mosaicing on subsequent tissue processing and H&E-stained frozen histology was minimal. There was no difference in the staining of the nuclear, cellular and dermal morphology between the frozen sections that were prepared before and after imaging. The acridine orange-staining process does not alter the tissue in any way and does not adversely affect the ability of subsequent H&E-stained frozen sections to deliver accurate clinical diagnoses. However, prolonged exposure of the tissue to relatively warm laboratory room temperature caused tissue degradation. Care was then taken to keep the excisions cool in isotonic saline solution before and after imaging and to expedite the reprocessing. This subsequently led to reproducible frozen sections for the remaining eight excisions.

Figure 8:
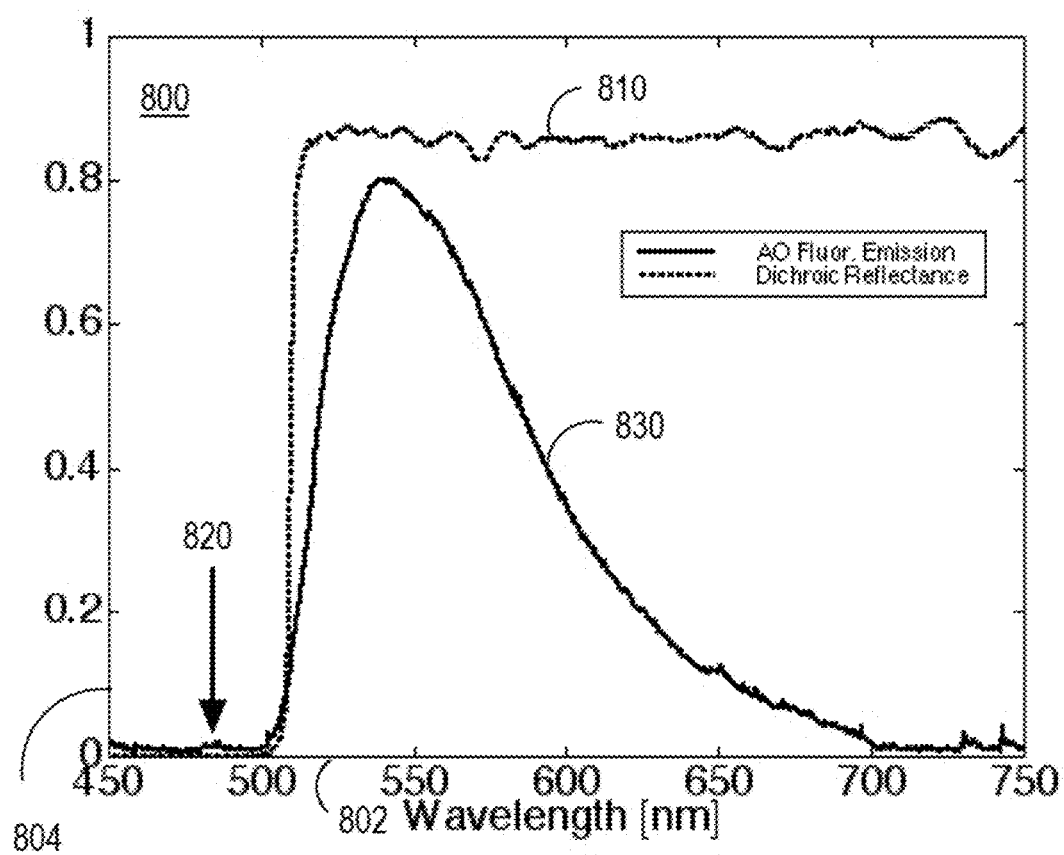
FIG. 8 is a graph that illustrates the detected fluorescence emission intensity, according to an embodiment.

FIG. 8 is a graph 800 that illustrates the detected fluorescence emission intensity, according to an embodiment. The horizontal axis 802 is optical wavelength in nanometers. The vertical axis 802 is intensity in arbitrary units. The reflection of the dichroic beamsplitter is indicted by curve 810. The fluorescence excitation wavelength at 488 nm is indicated by arrow 820. As can be seen, the dichroic beamsplitter does not reflect the excitation wavelength into the fluorescence channel. The fluorescence emissions intensity from the acridine orange dye is indicated by curve 830, and peaks at about 540 nm. As can be seen, the dichroic beamsplitter reflects the entire fluorescence wavelength range into the fluorescence channel.

As described above, the fluorescence emission intensity provides a strong contrast between the nucleus and cytoplasm of a cell and provides a good measure of tumor cells that cluster many nuclei in a small area. In addition to the nuclear/cytoplasmic contrast, Dermis is also dark leading to high nuclear/dermal contrast as well.

6. Multimodal Image Presentation

In another set of embodiments, a method for presenting a multimodal image includes illuminating a spot on a surface of a biological sample with a light beam using a confocal microscope. A first emission intensity from the spot is detected in a first range of optical properties, such as wavelength, polarization, and phase. A second emission intensity from the spot is detected in a second range of optical properties. A pixel that corresponds to the spot in an image is colored using a linear or other combination of the first emission intensity detected from the spot and the second emission intensity detected from the spot. In some of these embodiments, the pixel is colored to approximate a color produced by a histology section for tissue at the spot.

Figure 9:
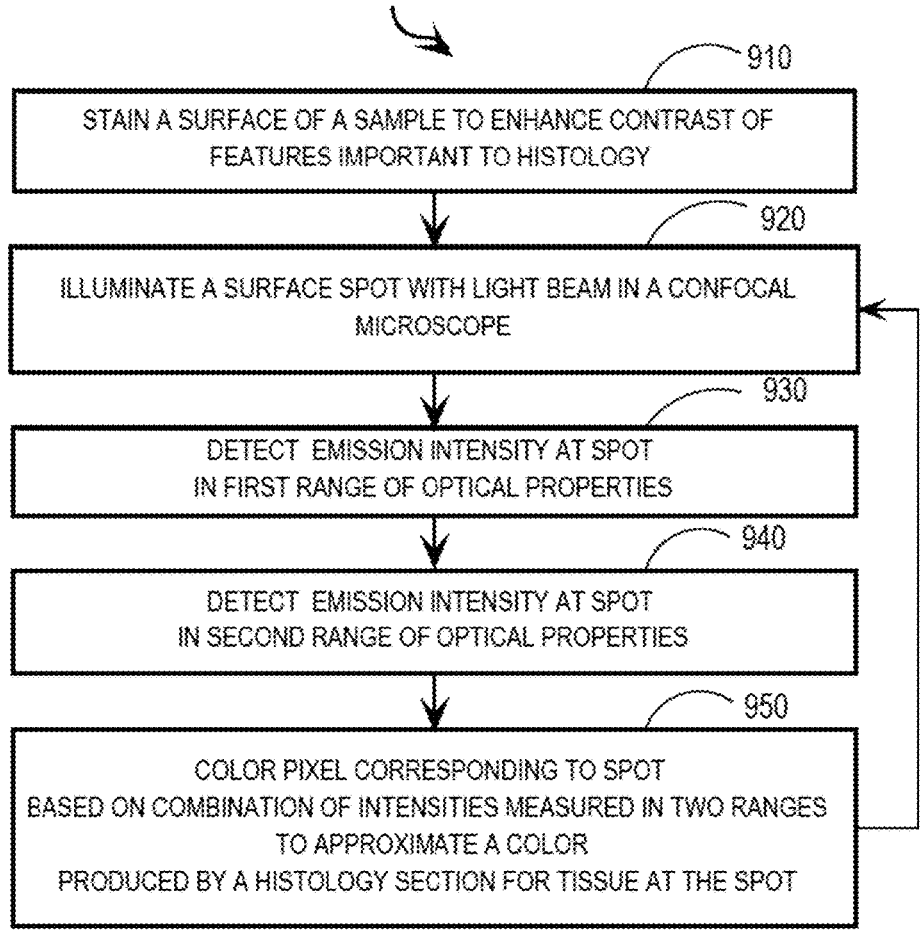
FIG. 9 is a flow diagram that illustrates at a high level a method to produce a multimodal image, according to an embodiment.

FIG. 9 is a flow diagram that illustrates at a high level a method 900 to produce a multimodal image, according to an embodiment. In step 910 a surface of a sample is stained to enhance contrast of features important to histology. For example, in some embodiments a Mohs surgery tissue excision is stained with acridine orange for 20 seconds. In some embodiments, no contrast enhancement is desired, and step 910 is omitted.

In step 920, a near-surface spot in the sample is illuminated with a light beam in a confocal microscope. For example, a near surface spot in the excised tissue stained with acridine orange is illuminated with a laser beam at wavelengths near 488 nm.

In step 930, emission intensity is detected from the spot in a first range of optical properties, such as polarization, wavelength and phase. For example, fluorescence emission intensity from the spot is measured in a wavelength range above about 500 nm.

In step 940, emission intensity is detected from the spot in a second range of optical properties. For example, reflectance emission intensity from the spot is measured in a wavelength range below about 500 nm, e.g., at 488 nm.

In step 950, a pixel corresponding to the spot is colored using a combination of the two intensities measured, such as a linear combination. For example, the pixel is colored to approximate the color of a frozen histology section for Mohs surgery excised tissue, as described below.

Histopathology with hematoxylin and eosin (H&E) is the most widely used tool for diagnosis and removal of cancer but it takes between a half-hour to days and requires expensive resources. The method described here employs multimodal confocal imagery based on luminescence to approximate H&E absorption stain, and is essentially free with the multimodal measurements and takes 5 minutes or less. Saving time saves the exposure of patients to infection and other surgical dangers as well as associated hospital costs.

The experiment described above shows equivalent sensitivity of the two techniques for BCC. Until this work, grayscale confocal images lack the structure-specific color-contrast that is conventionally provided by the use of two stains in histopathology: hematoxylin and eosin. Incorporating multimodality in the confocal microscopy enables independent measurements of the cellular morphology versus the reflective structure of collagen in the dermis. Combining multiple modes with mosaicing microscopy in Mohs surgery (MMMMM) demonstrates diagnostic ability previously limited to histopathology.

Two modes are combined, encoding color contrast. The cellular/dermis contrast is increased in the multimodal color images. Choosing colors such as the purple and pink of hematoxylin and eosin triggers conditioned recognition from pathologists and clinicians, making MMMMM accepted widely and rapidly. For more than 100 years, H&E staining has been used to independently label nuclei and collagen/cytoplasm. The reflectance and fluorescence modes of this embodiment accomplish the same stain/counter-stain task.

In biological tissues, collagen and cytoplasm scatter light. In confocal reflectance mode these components appear bright, whereas nuclei do not scatter light and appear dark. Unstained reflectance mode confocal microscopy therefore accomplishes the same function as Eosin.

Nuclear fluorescent stains (such as acridine orange) label only the DNA. Therefore, nuclei appear bright in fluorescence mode, whereas the cytoplasm and collagen (which do not have DNA) appear dark. The selective labeling of the nuclei in fluorescence mode therefore accomplishes the same function as hematoxylin.

The contrast of tumors using only the fluorescence mode is now improved so that the confocal microscopy parallels conventional histopathology. Nodular and micro-nodular tumors are readily detected while tiny infiltrative and sclerosing type tumors are detected at high magnification. Previous embodiments involving only fluorescence confocal imaging thus far have shown high sensitivity and specificity but have been accepted only by Mohs surgeons who have an intimate understanding of confocal optics and are accustomed to the grayscale fluorescence images. The embodiment described in this section makes confocal images readable by anyone familiar with H&E images (e.g., all pathologists and Mohs surgeons).

A multimodal confocal microscope (e.g., microscope 700 depicted in FIG. 7A) collected co-registered fluorescence and reflectance mosaics of excised skin cancer specimens. The grayscale reflectance and fluorescence mode images were combined by color coding and combining. Since pathologists are generally used to interpreting histopathology with hematoxylin and eosin staining, the purple and pink colors of these two dyes were adopted to maximize association with cells and non-cellular structures, respectively.

To acquire the respective red, green and blue (RGB) levels to produce these colors, a digital image was captured of a conventionally stained specimen. Sampling the image over areas of hematoxylin stained matter and eosin stained matter yielded brightness of the RGB pixels in hematoxylin areas [Hr Hg Hb]=[0.89 0.20 1] and in eosin areas [Er Eg Eb]=[1 0.55 0.88], respectively. The RGB values for hematoxylin are normalized to the blue level since the purple hue of the stain is farther blue-shifted and the values for eosin are normalized to the red level since the pinkish hue is red-shifted. Adopting the notation that the brightness levels for red, green and blue [r g b] correspond to the index k [k=1 k=2 k=3], respectively, and that the indices i and j refer to the column number and row number of a pixel location, a pseudo colored H&E imitating confocal image is computed according to Equation 1.

$$\text{image}_{i,j,k} = 1 - F_{i,j}(1-H_k) - R_{i,j}(1-E_k) \tag{1}$$

Where F is fluorescence brightness and R is reflectance brightness. The pseudo-colored image has the appropriate dimensions for export as an image file such as bitmap, TIF or JPEG.

Figure 10:
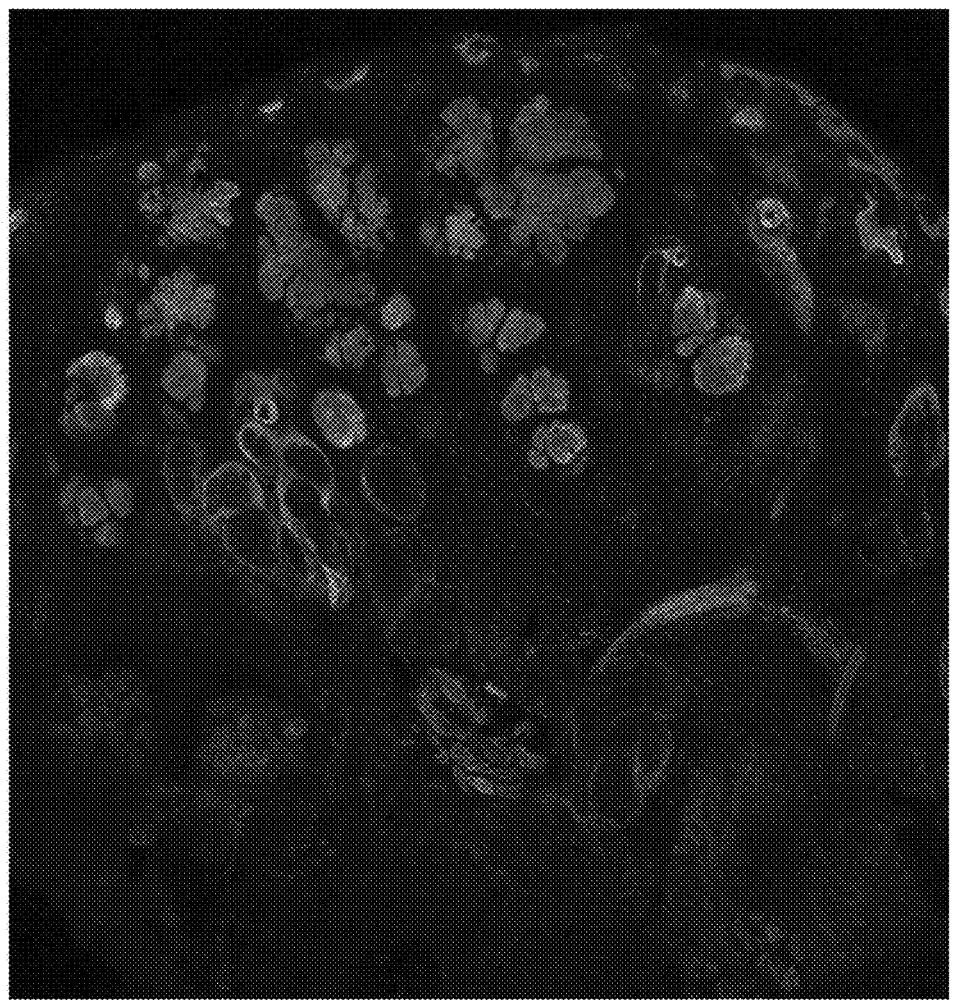
FIG. 10 is an image that illustrates the individual fluorescence mode of the microscope, according to an embodiment.
Figure 11:
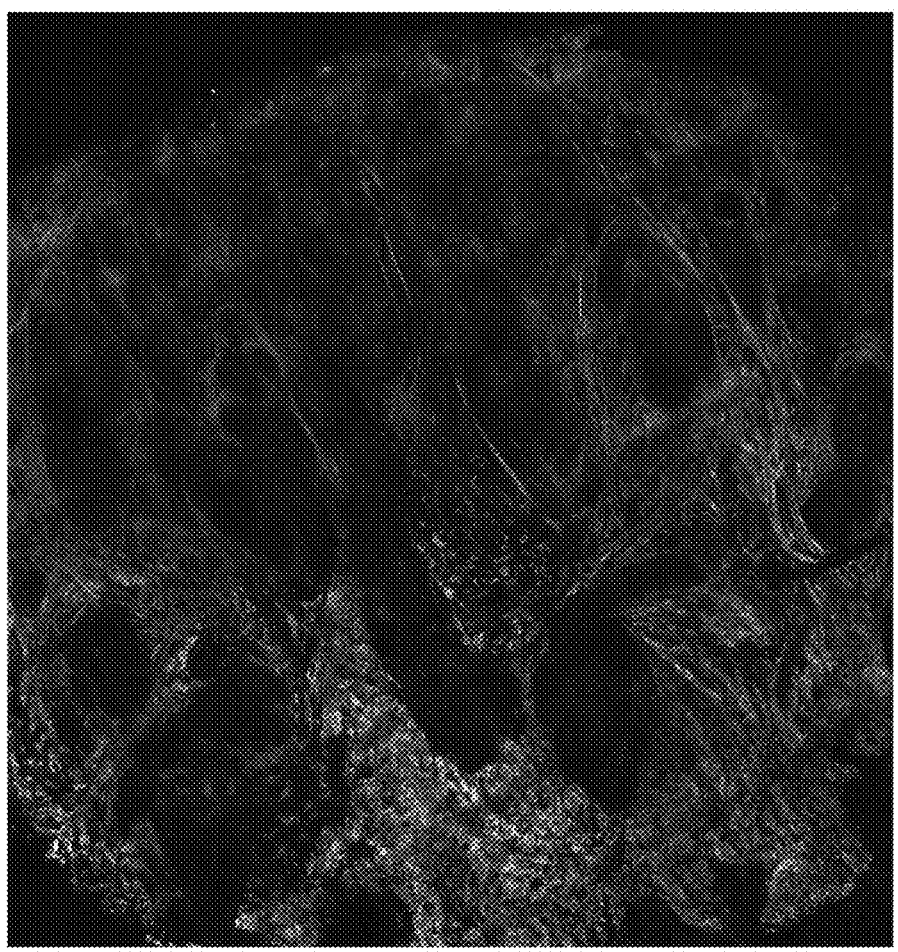
FIG. 11 is an image that illustrates the individual reflectance mode of the microscope on the same sample, according to an embodiment.
Figure 12:
FIG. 12 is an image that illustrates coloring of pixels to approximate histology, according to an embodiment.
Figure 13:
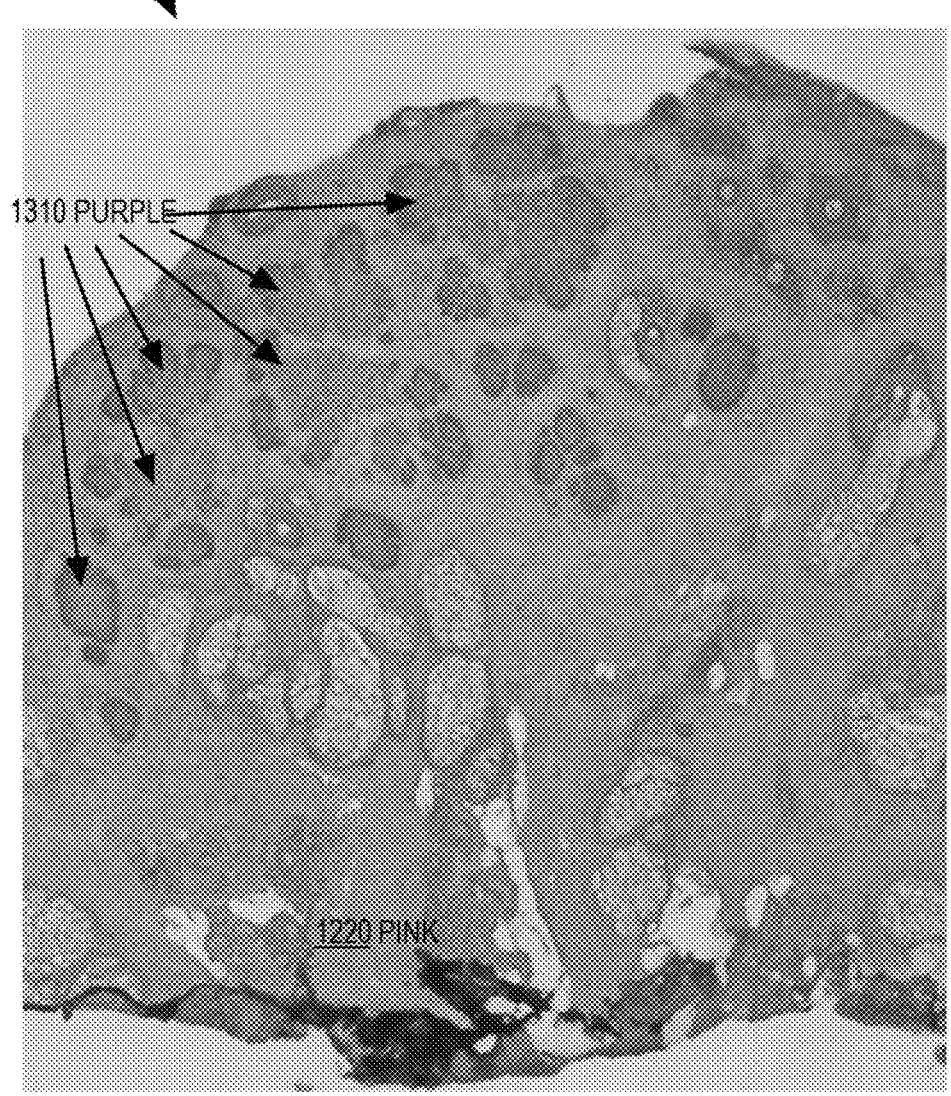
FIG. 13 is an image that illustrates example histology.
Figure 14:
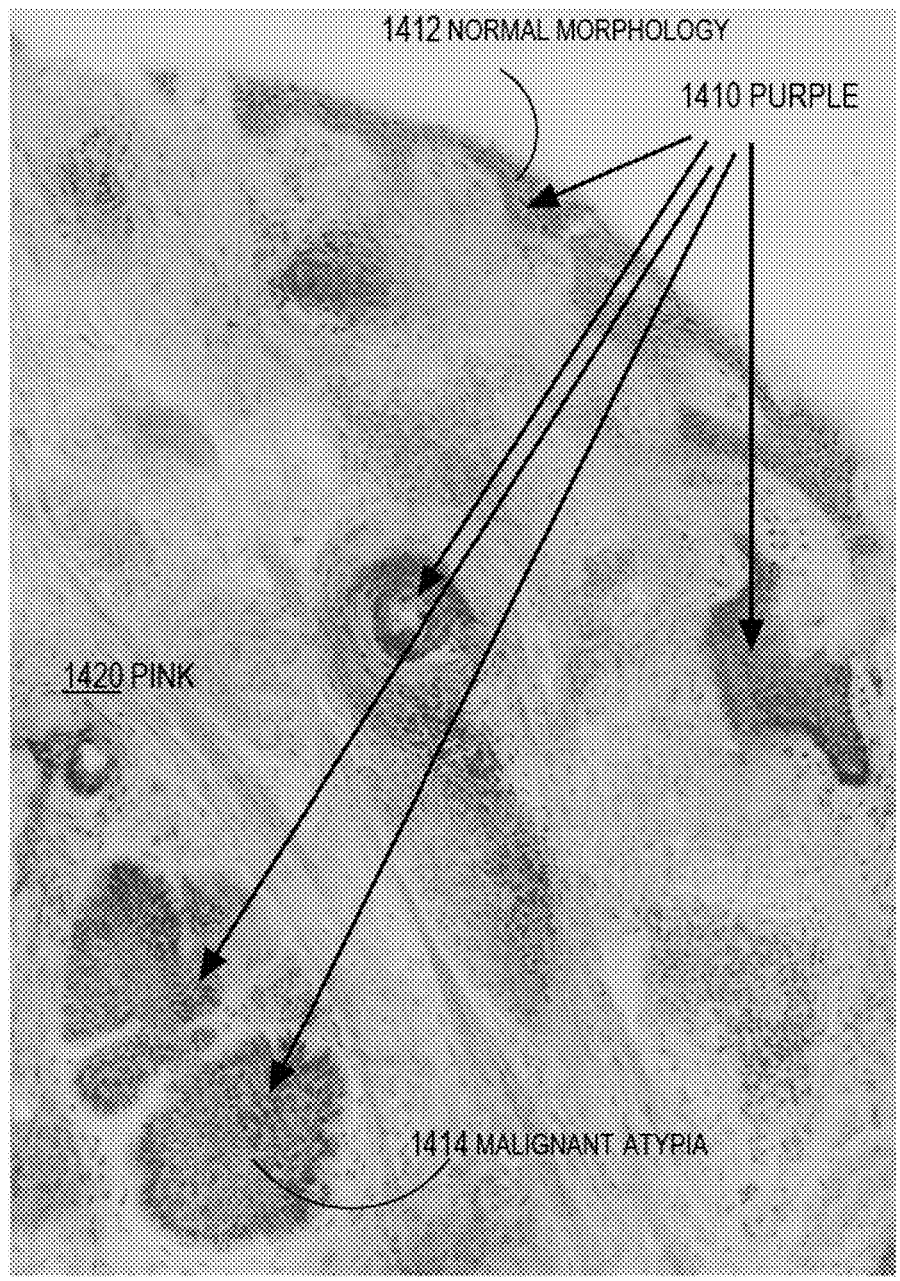
FIG. 14 is an image that illustrates a zoomed in portion of color image of FIG. 12, according to an embodiment.

In an illustrated embodiment, tissue biopsies are immersed in acridine orange for 20 seconds and imaged in 5 minutes. FIG. 10 is a mosaic image 1000 that illustrates the fluorescence mode of the microscope, according to an embodiment. FIG. 11 is a mosaic image 1100 that illustrates the individual reflectance mode of the microscope on the same sample, according to an embodiment. In FIG. 10 and FIG. 11, there is no color because each pixel is a simple measurement of intensity. These two images 1000 and 1100 are taken simultaneously and correlate spatially with respect to the sample. FIG. 12 is an image 1200 that illustrates coloring of pixels to approximate histology, according to an embodiment. The coloring shown is an implementation of equation 1 on the data of image 1000 and image 1100 to produce a color image 1200. Example purple areas 1210 and pink areas 1220 are indicated. FIG. 13 is an image 1300 that illustrates example histology. The histology section in image 1300, for comparison to image 1200, is the last frozen histology section taken from the excised tissue, a few millimeters from the surface of the sample scanned in image 1000 and 1100. Example purple areas 1310 and pink areas 1320 resulting from conventional H&E staining are indicated. FIG. 14 is an image 1400 that illustrates a zoomed in portion of color image 1200, according to an embodiment. Example purple areas 1410 and pink areas 1420 are indicated. Of the purple areas, normal morphology is evident in region 1412 and malignant atypia is evident in region 1414.

This technique converts luminous information (reflectance and fluorescence) to pigment (absorbance) based images. More generally, the technique comprises attaining the spectral properties of specific stains and encoding that information along with multimodal grayscale confocal images.

FIG. 7B is a block diagram that illustrates a multi modal reflectance/fluorescence confocal microscope 702, according to another embodiment. In this embodiment, the microscope 702 is configured to capture two independent fluorescence images, in addition to the reflectance image. In the illustrated embodiment, two laser sources are used to alternately illuminate the same scan. Laser source 710 is a 488 nm laser source that causes acridine orange (AO) dye to fluoresce, as in microscope 700. Laser source 711 is a 532 nm laser source that causes eosin (Eo) dye to fluoresce. The two beams are alternately input into the 7× beam expander 773 and subsequent optical components, described above for microscope 700, by controlling the acousto-optic deflector (AOD) 740, also called an acousto-optic modulator (AOM). In the illustrated embodiment, the AOD is controlled by toggle 741 that switches acoustic frequencies with each turn of the polygonal mirror 776. Thus each x direction scan by one laser is immediately followed by an x-direction scan by the other laser. To account for the double scanning, the galvo mirror 778 that scans in the perpendicular y direction is slowed by a factor of two as indicated by the component 775. In the illustrated embodiment the reflectance light from both lasers is detected by the reflectance detector (Det R) 742, such as $APD_R$ 722 and captured by frame grabber 762 and fed into computer 760 for assembly and storage. Similarly, light for both fluorescence scans are captured by the fluorescence detector (Det F) 743, such as $APD_F$ 738 and captured by frame grabber 763 and fed into computer 760 for assembly and storage. In this embodiment, the dichroic beamsplitter 734 to reflect only the fluorescence beam into the fluorescent channel passes light a wavelengths of 532 and below and reflects light at higher wavelengths, where the fluorescence occurs (about 550 nm and above for both AO and [for eosin). In another embodiment, the AOD 740 is controlled by computer 160 instead of toggle 741. An advantage of these embodiments is the precise and rapid control of the beams afforded by the AOD 740 compared to mechanical deflectors.

Figure 7C:
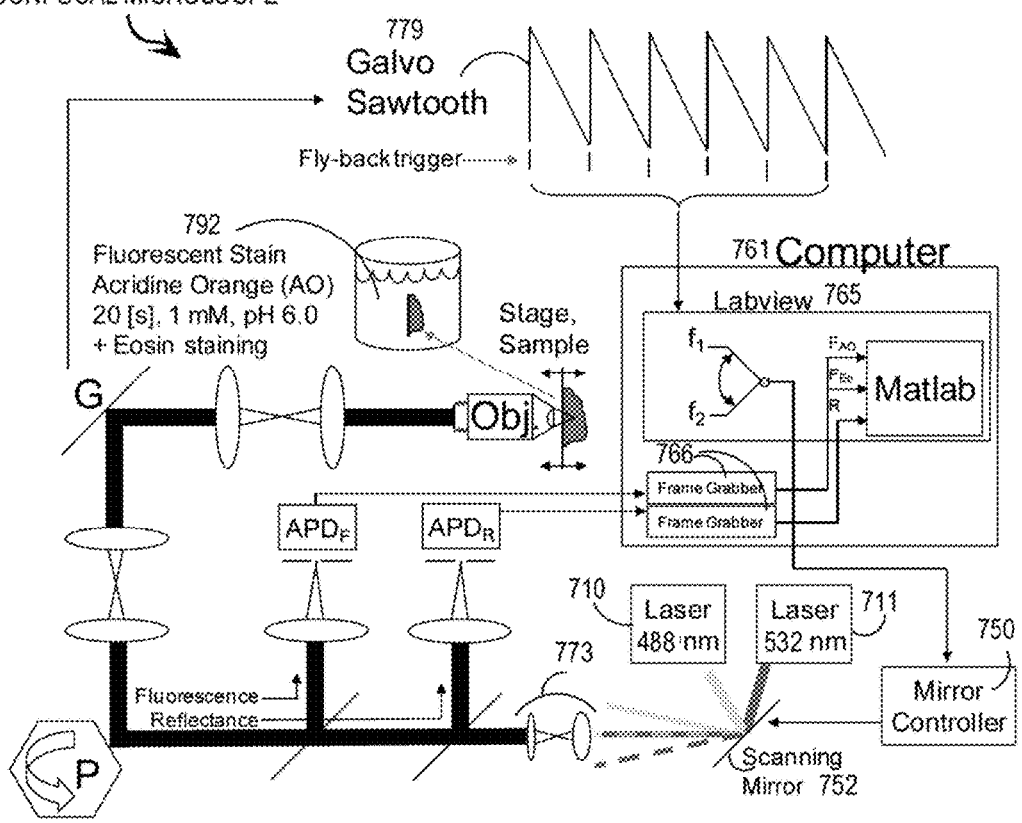
FIG. 7C is a block diagram that illustrates a multi modal reflectance/fluorescence confocal microscope, according to another embodiment.

FIG. 7C is a block diagram that illustrates a multi modal reflectance/fluorescence confocal microscope 704, according to another embodiment. In this embodiment, the microscope 704 is again configured to capture two independent fluorescence images, in addition to the reflectance image. In the illustrated embodiment, the same two laser sources 710 and 711 are used to alternately illuminate the same scan as in microscope 702 depicted in FIG. 7B. The two beams are alternately input into the 7× beam expander 773 and subsequent optical components, described above for microscope 700, by controlling a scanning mirror 752 with mirror controller 750. In the illustrated embodiment, the scanning controller 750 is controlled by computer 761 based on the galvo-sawtooth signal 779. Thus each x,y scan (image) by one laser is immediately followed by an x,y scan (image) by the other laser. Since whole images are collected between switching lasers, there is no need to separate interleaving scan lines, as in the configuration of microscope 702. $APD_F$ and $APD_R$ may be used to collect the images, as in microscope 700. In the illustrated embodiment the reflectance light from both lasers is detected by the reflectance detector $APD_R$ 722 and captured by software frame grabbers 766 in computer 761. Similarly, light for both fluorescence scans are captured by the fluorescence detector $APD_F$ 738 and captured by software frame grabber 766. An advantage of this approach is the low cost and current wide availability of scanning mirror 752. In another embodiment, an AOD, instead of scanning mirror controller 750, is controlled by computer 161.

Figure 17:
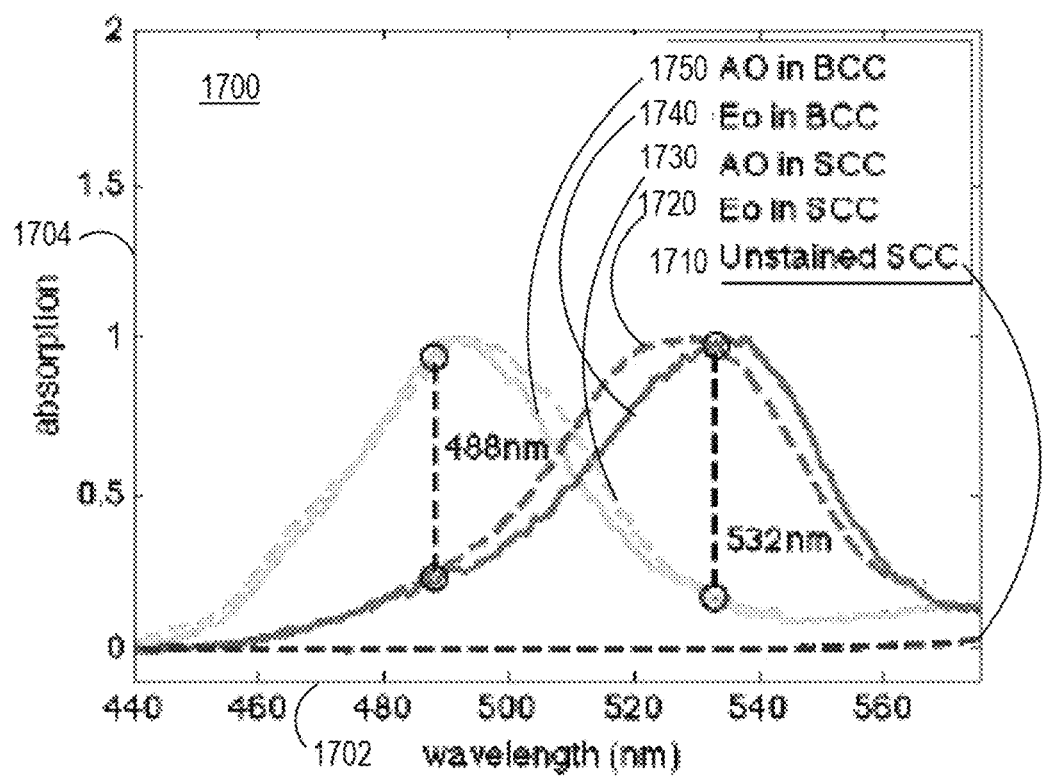
FIG. 17 is a graph that illustrates absorption profiles for two fluorescent stains, according to an embodiment.

FIG. 17 is a graph 1700 that illustrates absorption profiles for two fluorescent stains, according to an embodiment. The horizontal axis 1702 indicates wavelength in nanometers (nm); and vertical axis 1704 indicates absorption normalized to 1 for maximum absorption. Trace 1710 shows, for comparison, the level of autofluorescence of unstained tissue for squamous cell carcinoma (SCC). Trace 720 shows the absorption spectrum for eosin (Eo) dye in SCC (Eo fluoresces at a longer wavelength); and trace 730 shows the absorption spectrum for acridine orange (AO) dye in SCC (AO fluoresces at a longer wavelength, about 550 nm). The sample is a fresh human skin tumor. There is a clear separation of absorption wavelengths, so each can be excited independently by the laser wavelengths indicated by the vertical lines labeled 488 nm and 532 nm, respectively. AO dye is substantially excited by the 488 nm laser, while Eo is not. On the contrary, Eo dye is substantially excited by the 532 nm laser, while AO is not. The story is substantially the same staining a fresh human skin tumor of basal cell carcinoma (BCC). Trace 740 shows the absorption spectrum for eosin (Eo) dye in BCC; and trace 750 shows the absorption spectrum for acridine orange (AO) dye in BCC. Again, there is a clear separation of absorption wavelengths.

Thus, using microscope 702 or microscope 703, a useful colored image can be generated as follows. The surface of the biological sample is contacted with a solution of acridine orange and eosin. A spot is illuminated with a first light beam and a second light beam. The first light beam comprises a laser beam of wavelength about 488 nanometers, and the second light beam comprising a laser beam of wavelength about 532 nanometers. Detecting a first emission intensity comprises detecting fluorescence emission intensity from the spot in a wavelength range above about 500 nanometers to detect cell nuclei, and detecting a second emission intensity comprises detecting fluorescence emission intensity from the spot in a wavelength range above about 532 nanometers to detect cytoplasm and collagen. A pixel that corresponds to the spot in an image is colored using a linear combination of the first emission intensity detected from the spot and the second emission intensity detected from the spot.

FIG. 18 is a graph that illustrates coloring of pixels from two fluorescence images to approximate histology, according to an embodiment. FIG. 18 includes six images: image 1802, image 1804, image 1806, image 1812, image 1814 and image 1820, all providing a full-field view of a region 0.5 mm by 0.5 mm in a 30× objective. Image 1802 depicts AO fluorescence from 488 nm excitation. Image 1804 depicts Eo fluorescence from 532 nm excitation. Image 1806 depicts reflectance at 532 nm excitation. Image 1812 depicts false color (blue tint of intensity difference from image 1802) that indicates nuclei. Image 1814 depicts false color (red tint of intensity difference from image 1804) that indicates counterstain. Image 1820 depicts false color combination of image 1812 and 1814 to yield H&E equivalent image, with purple areas 1822 indicating nuclei and pink areas 1824 indicating collagen/cytoplasm.

7. Computer Hardware Overview

Figure 15:
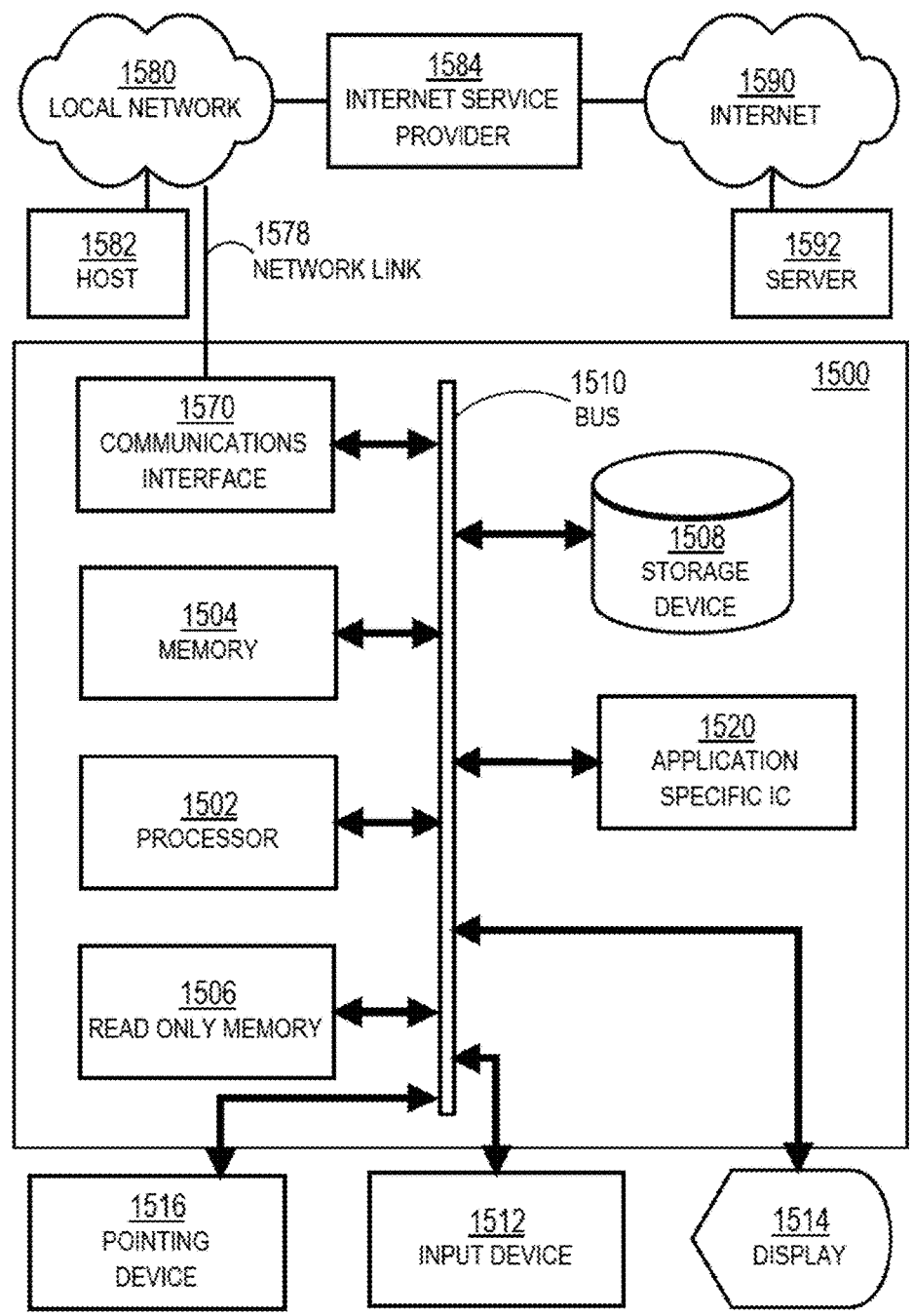
FIG. 15 is a block diagram that illustrates a computer system upon which an embodiment of the invention may be implemented.

FIG. 15 is a block diagram that illustrates a computer system 1500 upon which an embodiment of the invention may be implemented. Computer system 1500 includes a communication mechanism such as a bus 1510 for passing information between other internal and external components of the computer system 1500. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). A sequence of binary digits constitutes digital data that is used to represent a number or code for a character. A bus 1510 includes many parallel conductors of information so that information is transferred quickly among devices coupled to the bus 1510. One or more processors 1502 for processing information are coupled with the bus 1510. A processor 1502 performs a set of operations on information. The set of operations include bringing information in from the bus 1510 and placing information on the bus 1510. The set of operations also typically include comparing two or more units of information, shifting positions of units of information, and combining two or more units of information, such as by addition or multiplication. A sequence of operations to be executed by the processor 1502 constitute computer instructions.

Computer system 1500 also includes a memory 1504 coupled to bus 1510. The memory 1504, such as a random access memory (RAM) or other dynamic storage device, stores information including computer instructions. Dynamic memory allows information stored therein to be changed by the computer system 1500. RAM allows a unit of information stored at a location called a memory address to be stored and retrieved independently of information at neighboring addresses. The memory 1504 is also used by the processor 1502 to store temporary values during execution of computer instructions. The computer system 1500 also includes a read only memory (ROM) 1506 or other static storage device coupled to the bus 1510 for storing static information, including instructions, that is not changed by the computer system 1500. Also coupled to bus 1510 is a non-volatile (persistent) storage device 1508, such as a magnetic disk or optical disk, for storing information, including instructions, that persists even when the computer system 1500 is turned off or otherwise loses power.

Information, including instructions, is provided to the bus 1510 for use by the processor from an external input device 1512, such as a keyboard containing alphanumeric keys operated by a human user, or a sensor. A sensor detects conditions in its vicinity and transforms those detections into signals compatible with the signals used to represent information in computer system 1500. Other external devices coupled to bus 1510, used primarily for interacting with humans, include a display device 1514, such as a cathode ray tube (CRT) or a liquid crystal display (LCD), for presenting images, and a pointing device 1516, such as a mouse or a trackball or cursor direction keys, for controlling a position of a small cursor image presented on the display 1514 and issuing commands associated with graphical elements presented on the display 1514.

In the illustrated embodiment, special purpose hardware, such as an application specific integrated circuit (IC) 1520, is coupled to bus 1510. The special purpose hardware is configured to perform operations not performed by processor 1502 quickly enough for special purposes. Examples of application specific ICs include graphics accelerator cards for generating images for display 1514, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1500 also includes one or more instances of a communications interface 1570 coupled to bus 1510. Communication interface 1570 provides a two-way communication coupling to a variety of external devices that operate with their own processors, such as printers, scanners and external disks. In general the coupling is with a network link 1578 that is connected to a local network 1580 to which a variety of external devices with their own processors are connected. For example, communication interface 1570 may be a parallel port or a serial port or a universal serial bus (USB) port on a personal computer. In some embodiments, communications interface 1570 is an integrated services digital network (ISDN) card or a digital subscriber line (DSL) card or a telephone modem that provides an information communication connection to a corresponding type of telephone line. In some embodiments, a communication interface 1570 is a cable modem that converts signals on bus 1510 into signals for a communication connection over a coaxial cable or into optical signals for a communication connection over a fiber optic cable. As another example, communications interface 1570 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1570 sends and receives electrical, acoustic or electromagnetic signals, including infrared and optical signals, that carry information streams, such as digital data.

The term computer-readable medium is used herein to refer to any medium that participates in providing information to processor 1502, including instructions for execution. Such a medium may take many forms, including, but not limited to, non-volatile media, volatile media and transmission media. Non-volatile media include, for example, optical or magnetic disks, such as storage device 1508. Volatile media include, for example, dynamic memory 1504. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1502 excluding transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Network link 1578 typically provides information communication through one or more networks to other devices that use or process the information. For example, network link 1578 may provide a connection through local network 1580 to a host computer 1582 or to equipment 1584 operated by an Internet Service Provider (ISP). ISP equipment 1584 in turn provides data communication services through the public, world-wide packet-switching communication network of networks now commonly referred to as the Internet 1590. A computer called a server 1592 connected to the Internet provides a service in response to information received over the Internet. For example, server 1592 provides information representing video data for presentation at display 1514.

The invention is related to the use of computer system 1500 for implementing the techniques described herein. According to one embodiment of the invention, those techniques are performed by computer system 1500 in response to processor 1502 executing one or more sequences of one or more instructions contained in memory 1504. Such instructions, also called software and program code, may be read into memory 1504 from another computer-readable medium such as storage device 1508. Execution of the sequences of instructions contained in memory 1504 causes processor 1502 to perform the method steps described herein. In alternative embodiments, hardware, such as application specific integrated circuit 1520, may be used in place of or in combination with software to implement the invention. Thus, embodiments of the invention are not limited to any specific combination of hardware and software.

The signals transmitted over network link 1578 and other networks through communications interface 1570, carry information to and from computer system 1500. Computer system 1500 can send and receive information, including program code, through the networks 1580, 1590 among others, through network link 1578 and communications interface 1570. In an example using the Internet 1590, a server 1592 transmits program code for a particular application, requested by a message sent from computer 1500, through Internet 1590, ISP equipment 1584, local network 1580 and communications interface 1570. The received code may be executed by processor 1502 as it is received, or may be stored in storage device 1508 or other non-volatile storage for later execution, or both. In this manner, computer system 1500 may obtain application program code in the form of a signal on a carrier wave.

Various forms of computer readable media may be involved in carrying one or more sequence of instructions or data or both to processor 1502 for execution. For example, instructions and data may initially be carried on a magnetic disk of a remote computer such as host 1582. The remote computer loads the instructions and data into its dynamic memory and sends the instructions and data over a telephone line using a modem. A modem local to the computer system 1500 receives the instructions and data on a telephone line and uses an infra-red transmitter to convert the instructions and data to a signal on an infra-red a carrier wave serving as the network link 1578. An infrared detector serving as communications interface 1570 receives the instructions and data carried in the infrared signal and places information representing the instructions and data onto bus 1510. Bus 1510 carries the information to memory 1504 from which processor 1502 retrieves and executes the instructions using some of the data sent with the instructions. The instructions and data received in memory 1504 may optionally be stored on storage device 1508, either before or after execution by the processor 1502.

8. Extensions and Alternative

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for presenting a multimodal image from a confocal microscope comprising:

contacting a surface of a biological sample with a solution of a first fluorescent stain that stains and distinguishes a nucleus of a cell;

illuminating a spot on a surface of the biological sample with a light beam using a confocal microscope;

detecting a first emission intensity from the spot in a first range of optical properties wherein the first emission intensity is intensity from the fluorescent stain;

detecting a second emission intensity from the spot in a second range of optical properties wherein the second emission intensity is intensity of unstained reflectance;

coloring a pixel that corresponds to the spot in an image using a linear combination of the first emission intensity detected from the spot and the second emission intensity detected from the spot, wherein the linear combination includes the first emission intensity times non-zero first factors in a red channel, green channel and blue channel, respectively, to imitate a purple stain of a hematoxylin dye and the second emission intensity times non-zero second factors in the red channel, green channel and blue channel, respectively, to imitate a pink stain of an eosin dye; and presenting the colored pixels on a display device to approximate the color produced by a conventional histology section for the biological sample at the spot;

wherein the first fluorescent stain diffuses in the biological sample to a depth of at least 30 microns within about 20 seconds of initial contact.

2. A method as recited in claim 1, wherein contacting the surface of the biological sample with the solution of the first fluorescent stain further comprising contacting the surface of the biological sample with the solution of the first fluorescent stain for a duration in a range from about 0.6 milliseconds to about 20 seconds.

3. A method as recited in claim 1, wherein contacting the surface of the biological sample with the solution of the first fluorescent stain further comprising contacting the surface of the biological sample with the solution of the first fluorescent stain for a duration sufficient to stain to a depth of about 30 microns.

4. The method as recited in claim 1, wherein:

the first fluorescent stain is acridine orange;

illuminating the spot further comprises illuminating the spot with a laser beam of wavelength about 488 nanometers (nm, 1 nm=$10^{-9}$ meters);

detecting the first emission intensity further comprises detecting a fluorescence emission intensity from the spot in a wavelength range above 500 nm; and detecting the second emission intensity further comprises detecting reflectance emission intensity from the spot in a wavelength range below 500 nm.

5. A method as recited in claim 1, further comprising contacting the surface of the biological sample with a solution of acetic acid to enhance contrast between cell nuclei and surrounding material.

6. A method as recited in claim 1, wherein coloring the pixel further comprises adding 100% intensity and subtracting the fluorescence emission intensity and subtracting the reflectance emission intensity for each color component of the pixel, whereby a pixel with no reflectance and no fluorescence appears white.

7. The method as recited in claim 1, wherein:

contacting the surface of the biological sample with the solution of the first fluorescent stain that contrasts the nucleus of the cell further comprises contacting the surface of the biological sample with a solution of eosin;

the method further comprises detecting a fluorescence emission intensity from the spot at a wavelength of about 532 nanometers (nm, 1 nm=$10^{-9}$ meters);

illuminating the spot further comprises illuminating the spot with a first laser beam of wavelength about 488 nm and with a second laser beam of wavelength about 532 nm; and detecting the first emission intensity further comprises detecting a fluorescence emission intensity from the spot at a wavelength of about 550 nm.

8. The method as recited in claim 7, further comprising detecting a reflectance emission intensity from the spot in a wavelength range that corresponds to a wavelength range of at least one of the first laser beam or the second laser beam.

9. A non-transitory computer-readable storage medium carrying one or more sequences of instructions for correcting illumination in images from a confocal microscope, wherein execution of the one or more sequences of instructions by one or more processors causes the one or more processors to perform the steps of:

receiving data that indicates a first emission intensity in a first range of optical properties from a spot on a surface of a biological sample contacted with a solution of a first fluorescent stain that stains and distinguishes a nucleus of a cell and illuminated with a light beam using a confocal microscope, wherein the first emission intensity is intensity from the fluorescent stain;

receiving data that indicates a second emission intensity from the spot in a second range of optical properties, wherein the second emission intensity is intensity of unstained reflectance;

determining a color for a pixel that corresponds to the spot in an image using a linear combination of the first emission intensity from the spot and the second emission intensity from the spot, wherein the linear combination includes the first emission intensity times non-zero first factors in a red channel, green channel and blue channel, respectively, to imitate a purple stain of a hematoxylin dye and the second emission intensity times non-zero second factors in the red channel, green channel and blue channel, respectively, to imitate a pink stain of an eosin dye; and presenting the colored pixels on a display device to approximate the color produced by a conventional histology section for the biological sample at the spot;

wherein the first fluorescent stain diffuses in the biological sample to a depth of at least 30 microns within about 20 seconds of initial contact.

* * * * *